United States Patent [19]
Rose

[11] 3,964,467

[45] *June 22, 1976

[54] METHODS AND APPARATUS FOR AUGMENTATION OF THE PRODUCTION OF ANTI-BODIES IN ANIMALS AND HUMANS AND THE COLLECTION THEREOF

[75] Inventor: Sam Rose, Eggertsville, N.Y.

[73] Assignee: BIO Response Inc., Scarborough, N.Y.

[ * ] Notice: The portion of the term of this patent subsequent to Mar. 6, 1990, has been disclaimed.

[22] Filed: Apr. 9, 1973

[21] Appl. No.: 349,330

Related U.S. Application Data

[60] Continuation-in-part of Ser. No. 328,048, Jan. 30, 1973, which is a division of Ser. No. 136,476, April 22, 1971, Pat. No. 3,179,182.

[52] U.S. Cl. .............................. 128/1 R; 195/1.7; 424/85; 424/101
[51] Int. Cl.² ........................................ A61B 19/00
[58] Field of Search .................. 128/1 R, 214 R; 195/1.7; 424/85, 101

[56] References Cited
UNITED STATES PATENTS

3,511,238   5/1970   Von Wrangell .................. 128/214 R
3,719,182   3/1973   Rose .................................. 128/1 R Primary Examiner—Dalton C. Truluck

[57] ABSTRACT

A process for augmenting production of a specific antibody from a patient including the steps of administering a specific antigen to the patient to cause production of the specific antibody, or choosing a subject containing an antigen, e.g., cancer, or one already immunized or making antibodies to an endogenous or exogenous antigen, performing a thoracic duct fistula on the patient, raising the central venous pressure of the patient for example, by pericordial tamponde, and collecting lymph from the fistula, centrifuging the collected lymph to separate the lymph cells therein from the lymph fluid, and to form a thin elongated layer of the separated cells, treating the thin elongated layer of lymph cells to assure that they are substantially free of the specific antibody produced, dispersing the cells in a physiologically balanced saline solution and returning the dispersed cells and solution to the patient intravascularly, and giving appropriate replacement therapy to maintain normal control and health of all other systems in the body, the replacement therapy comprising fluids which can be of several kinds, but having in common that they are substantially free of the specific antibody.

45 Claims, 20 Drawing Figures

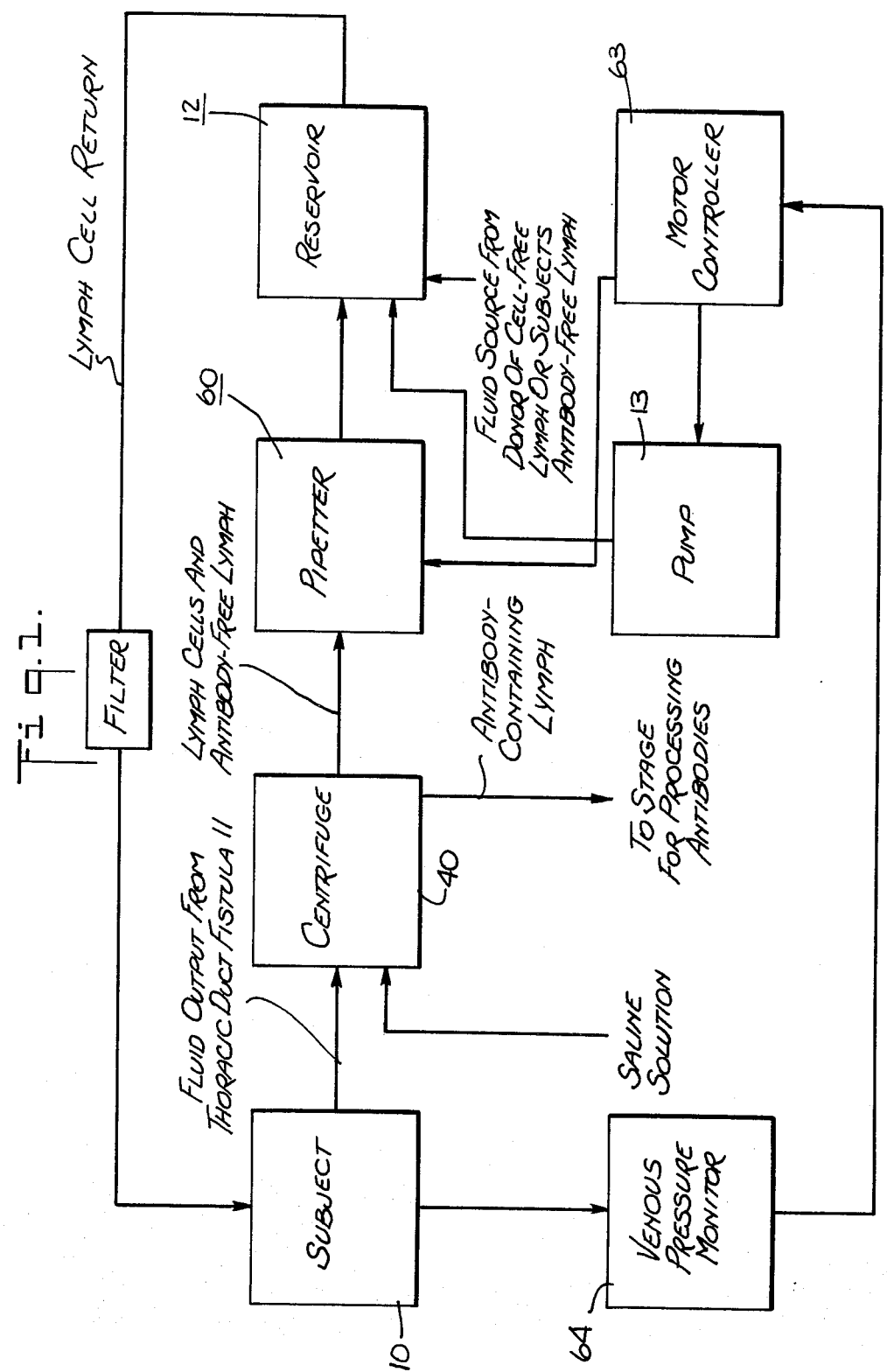

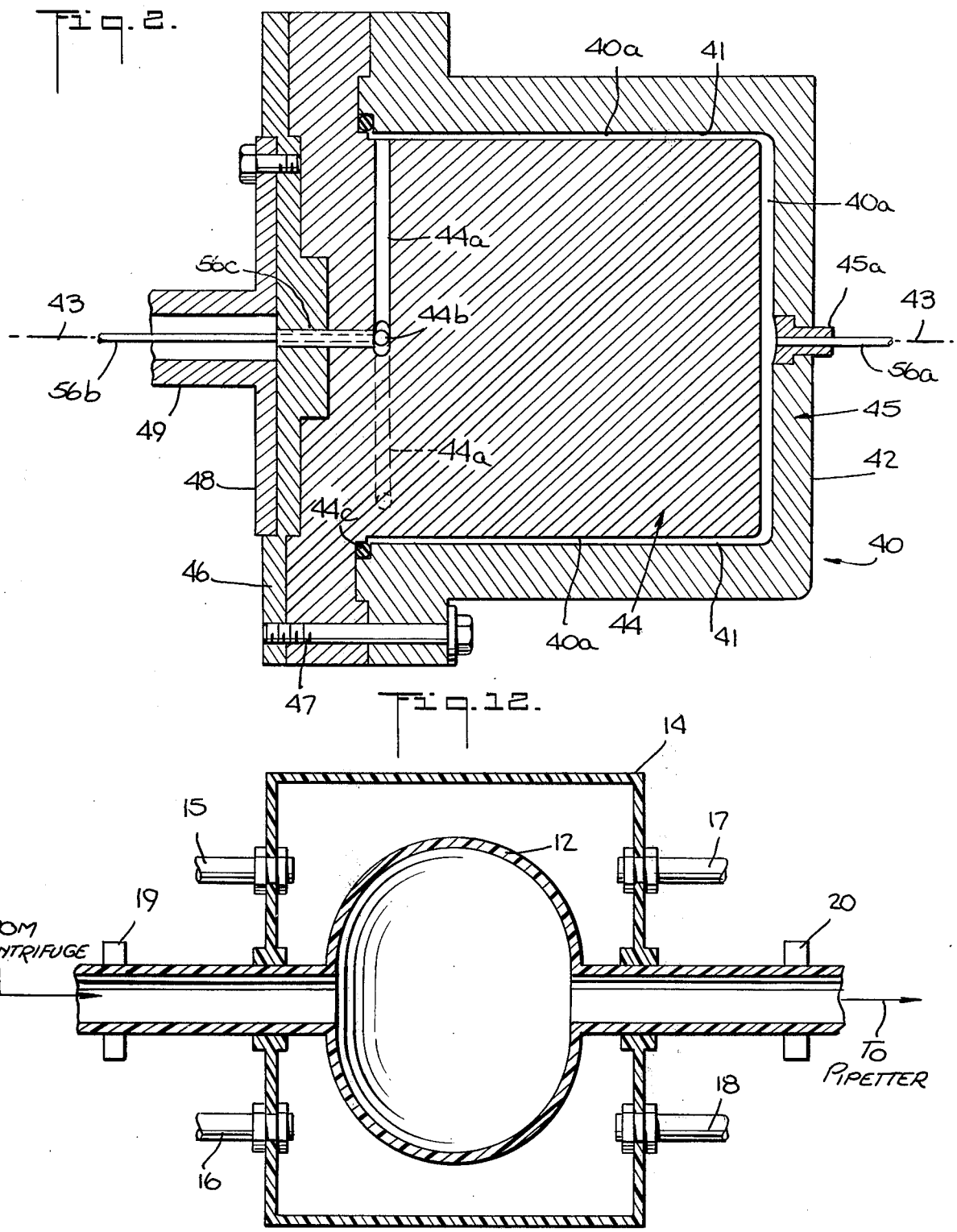

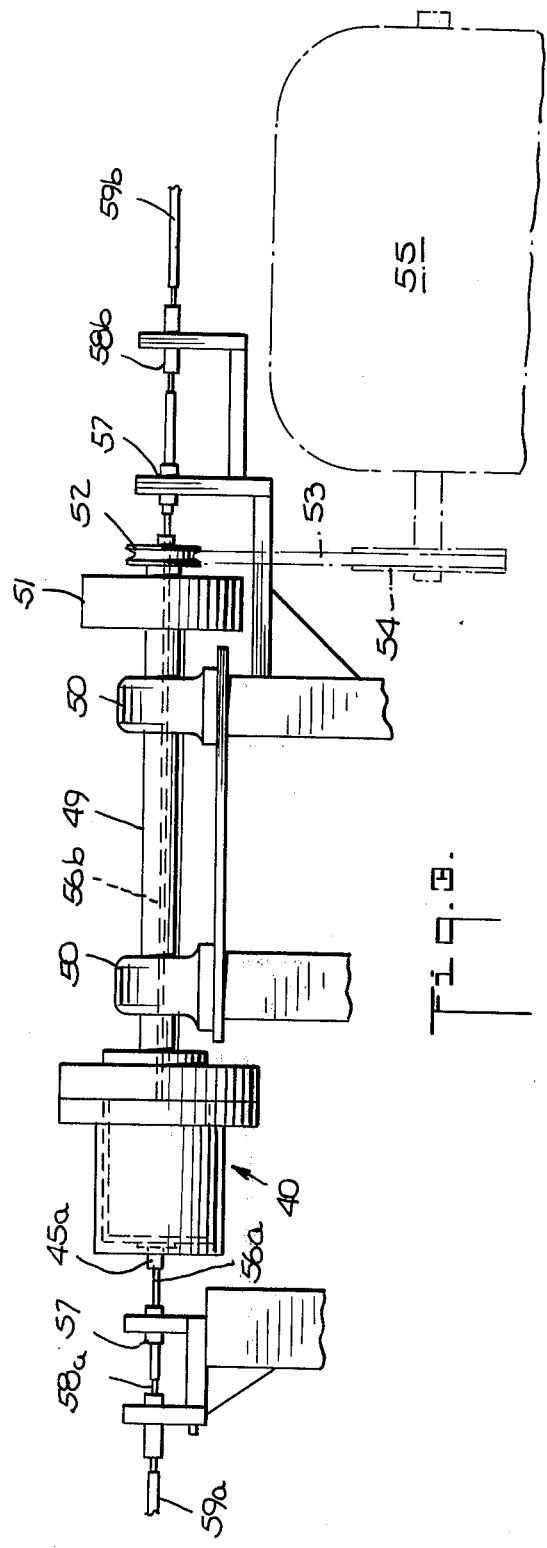
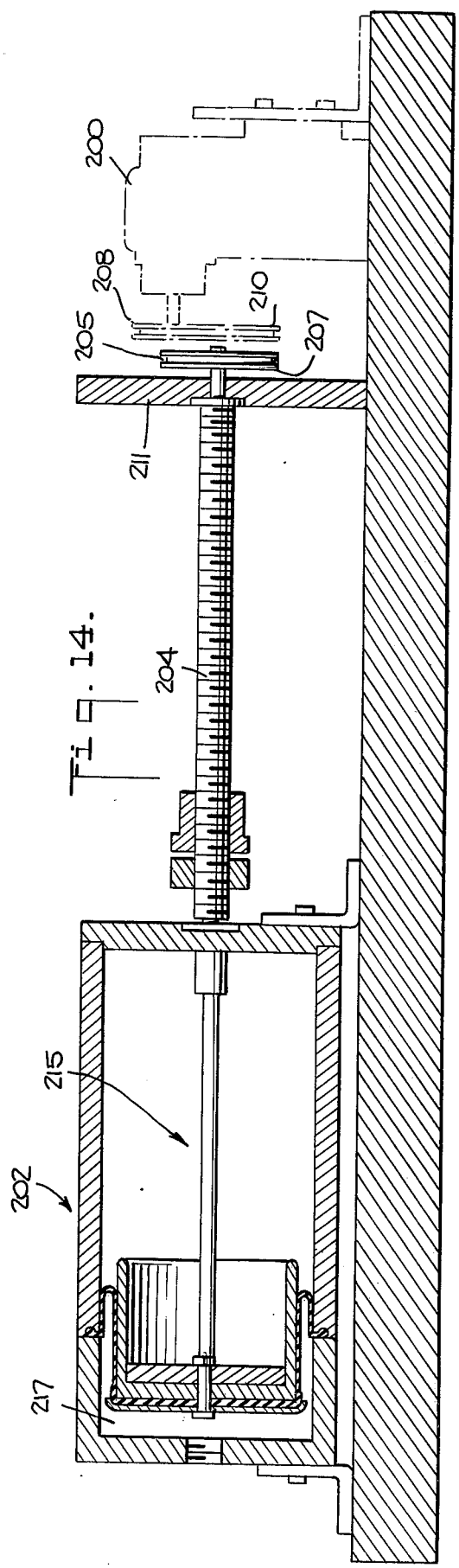

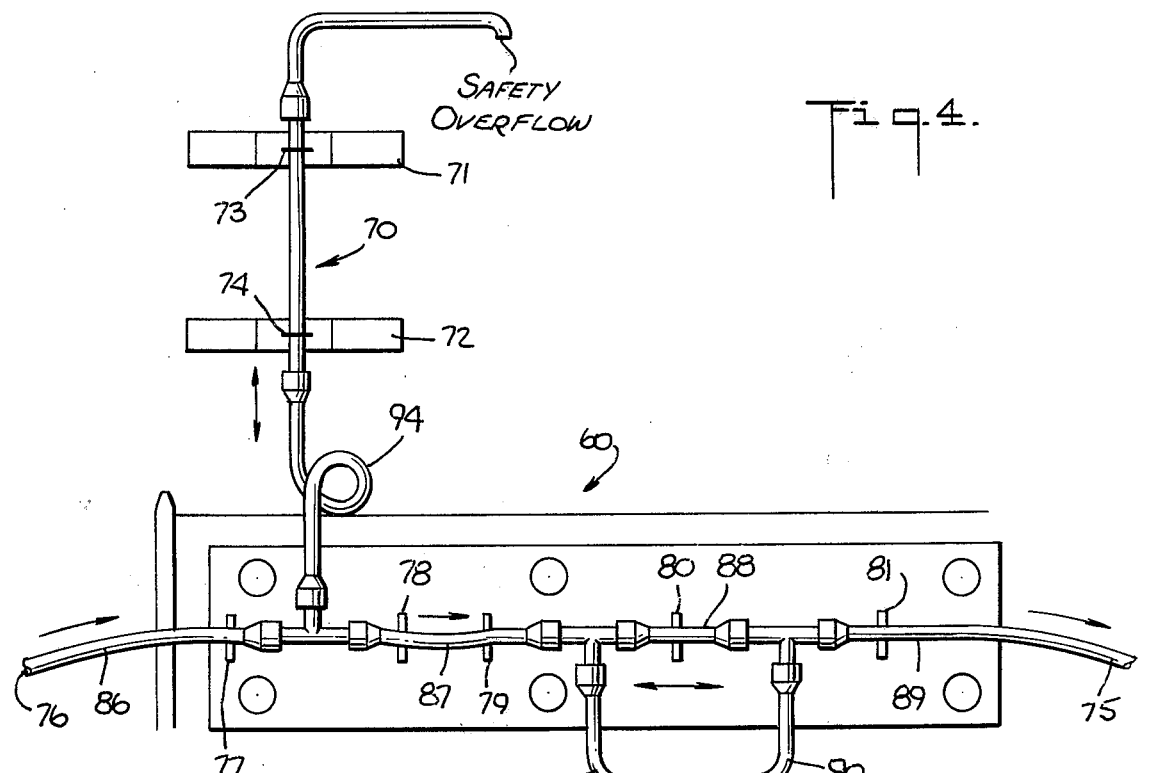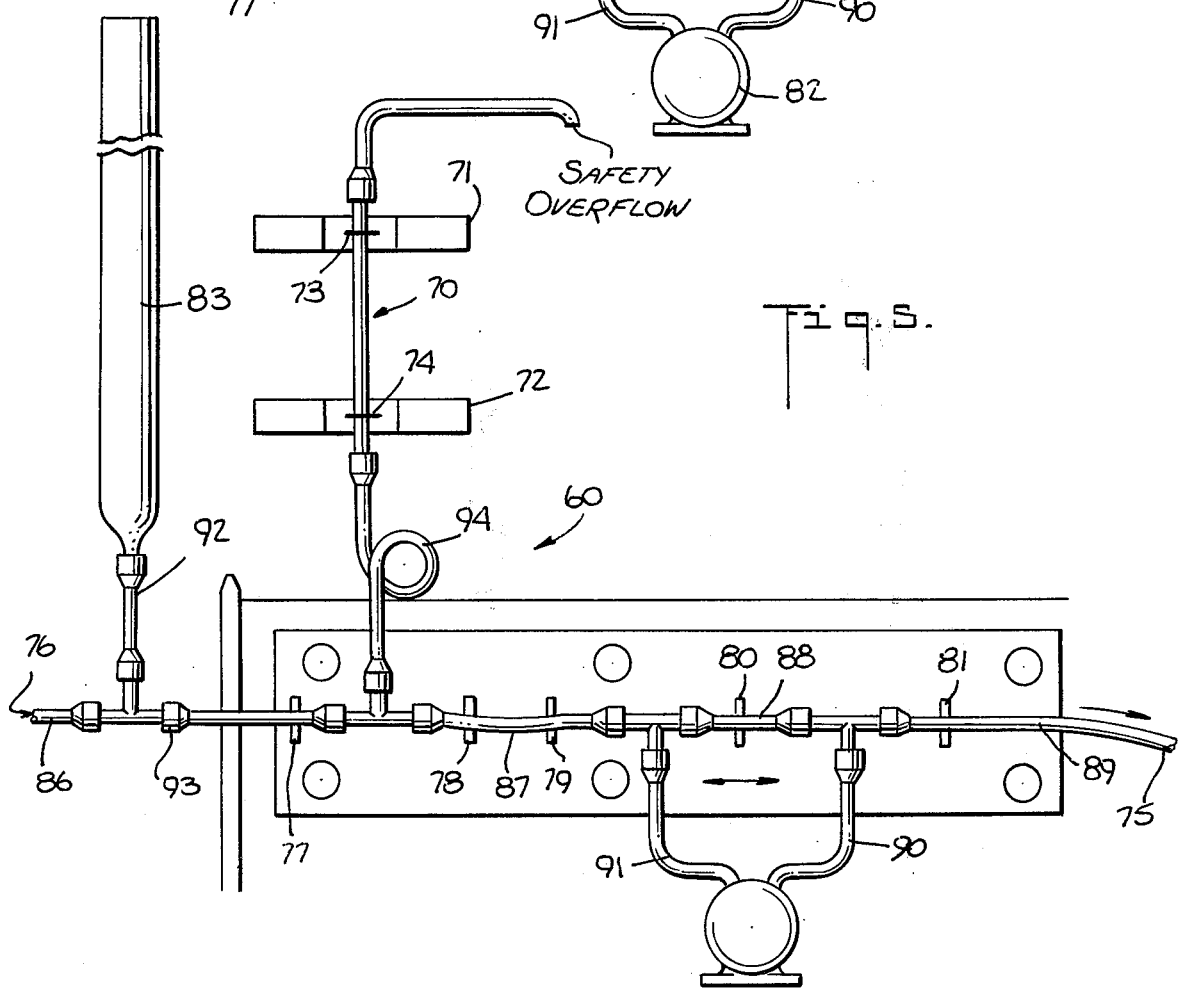

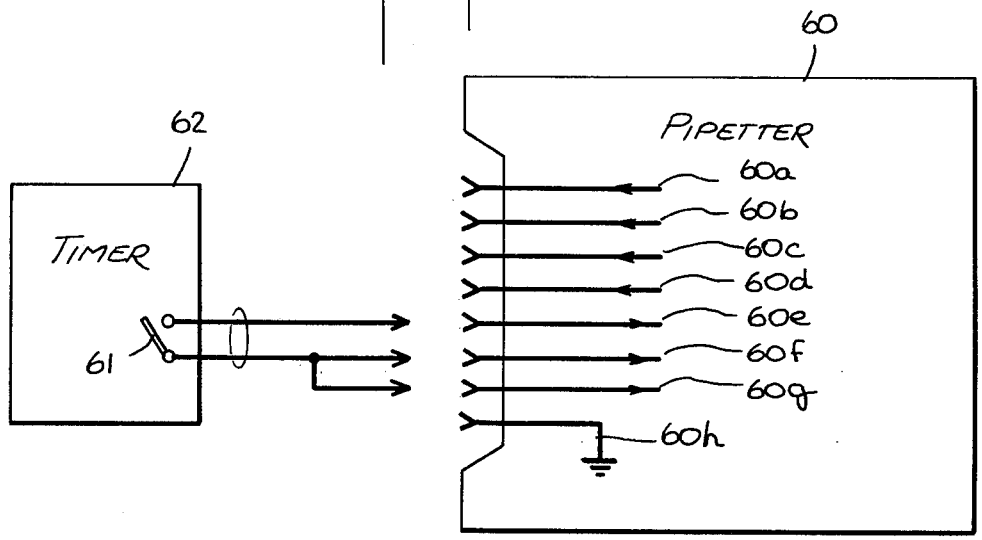
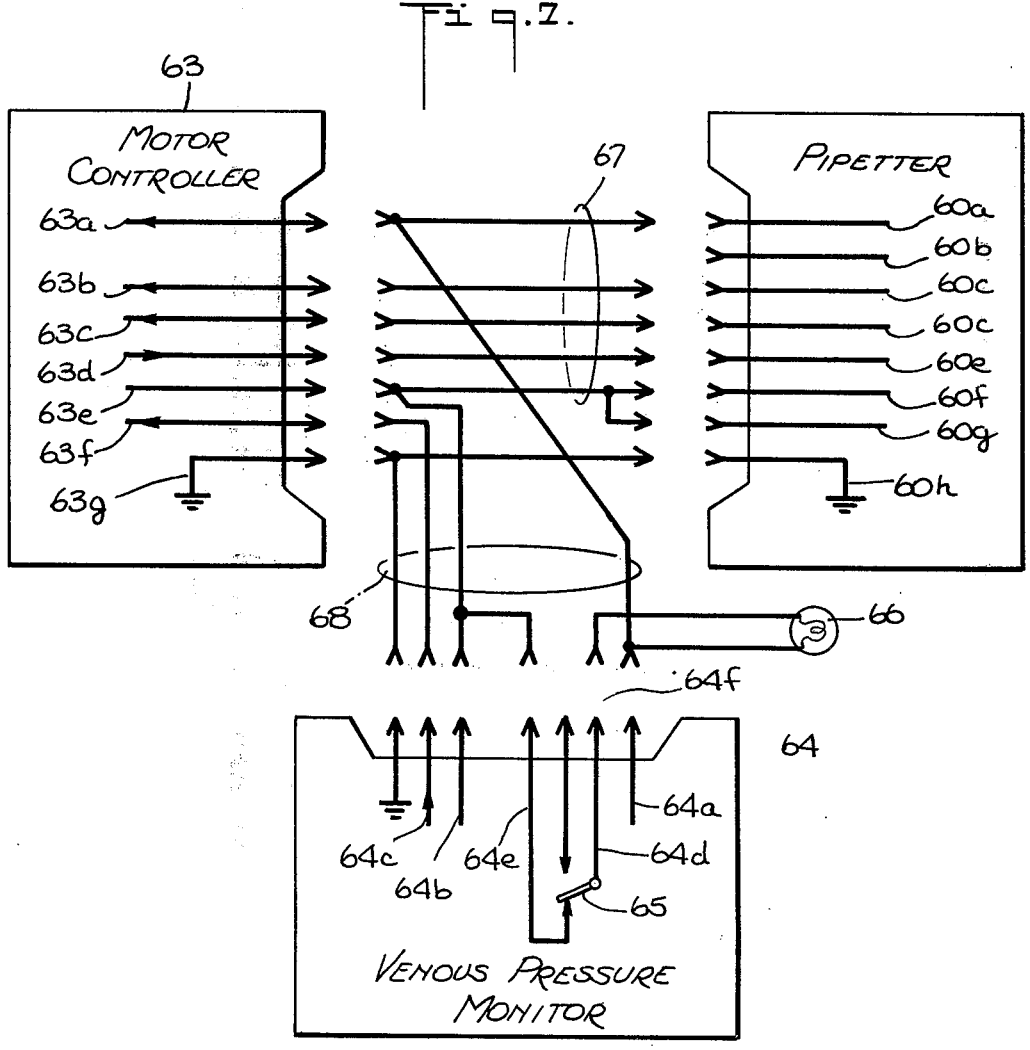

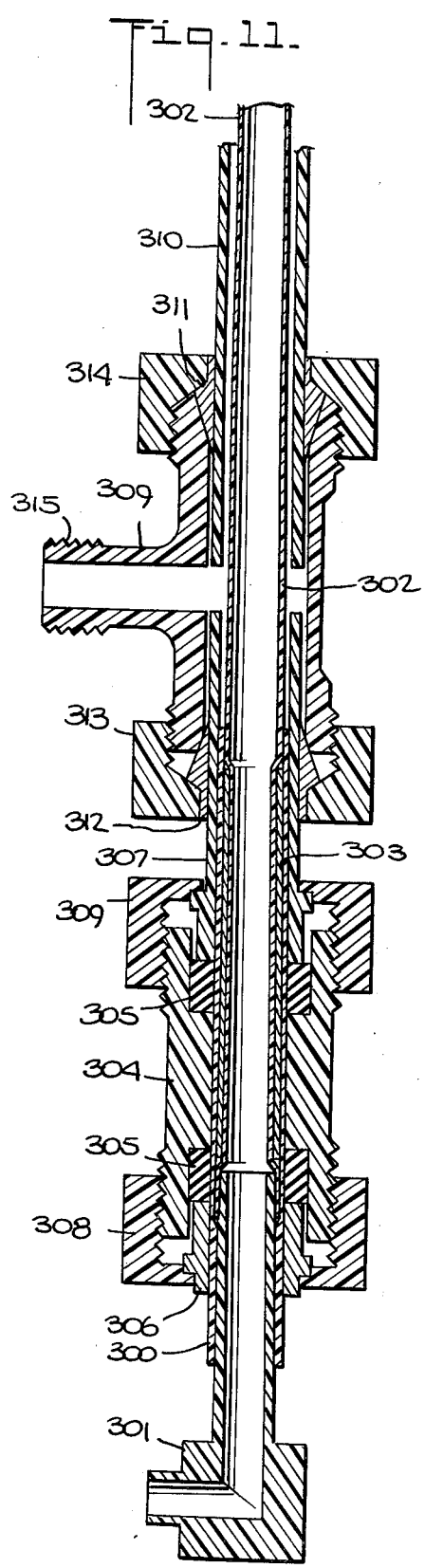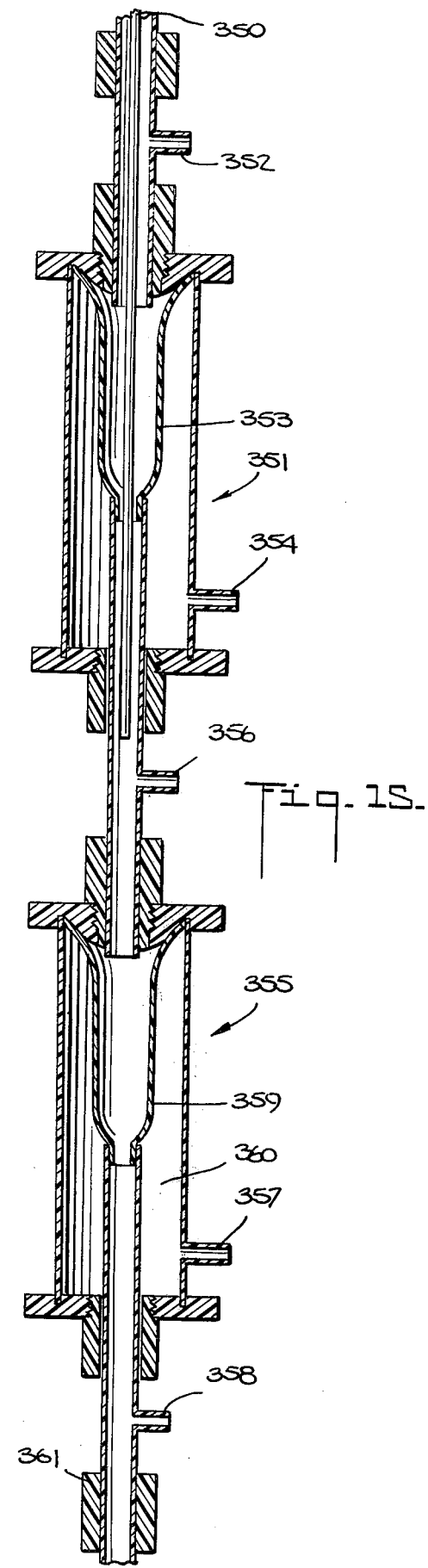

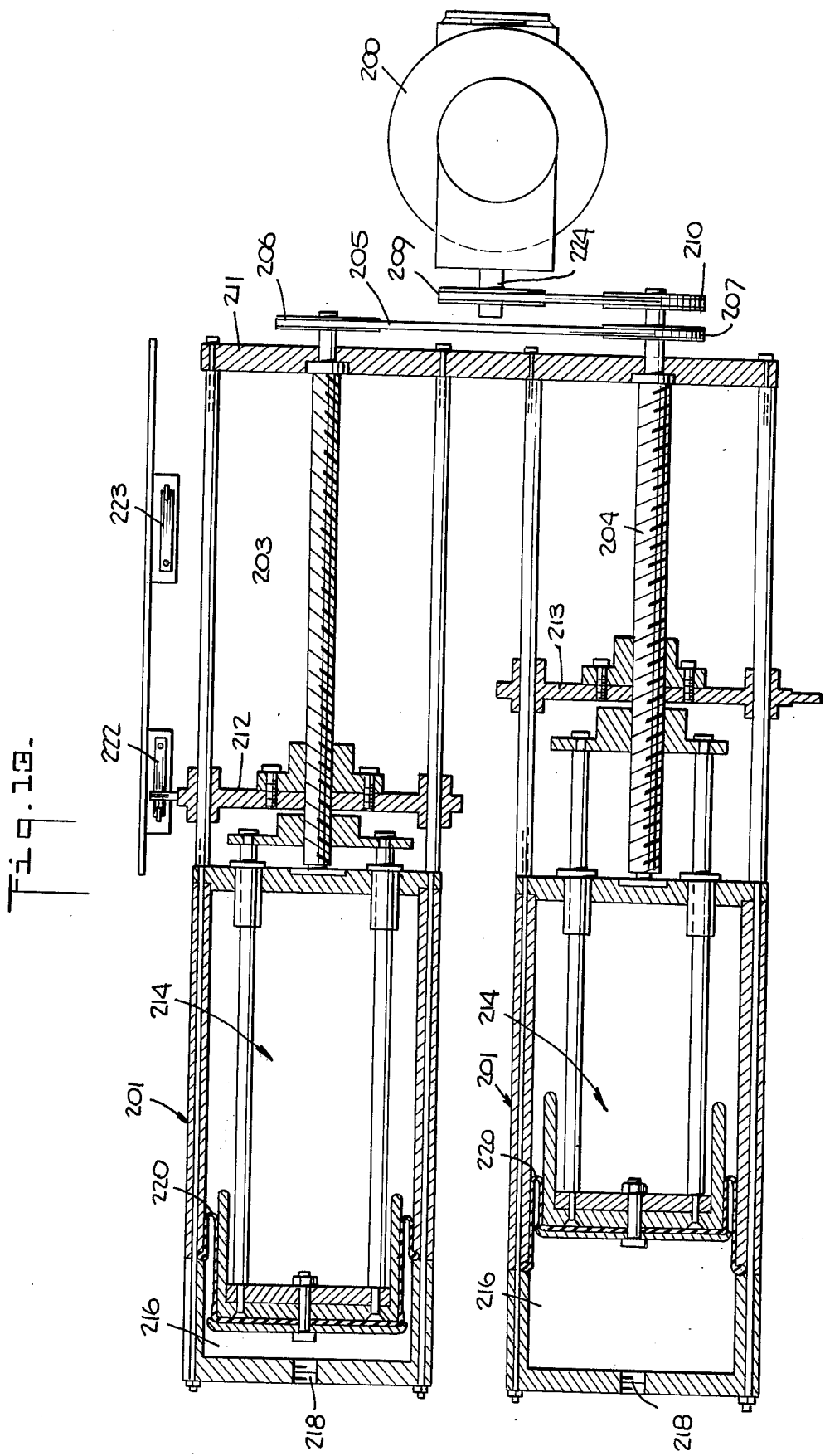

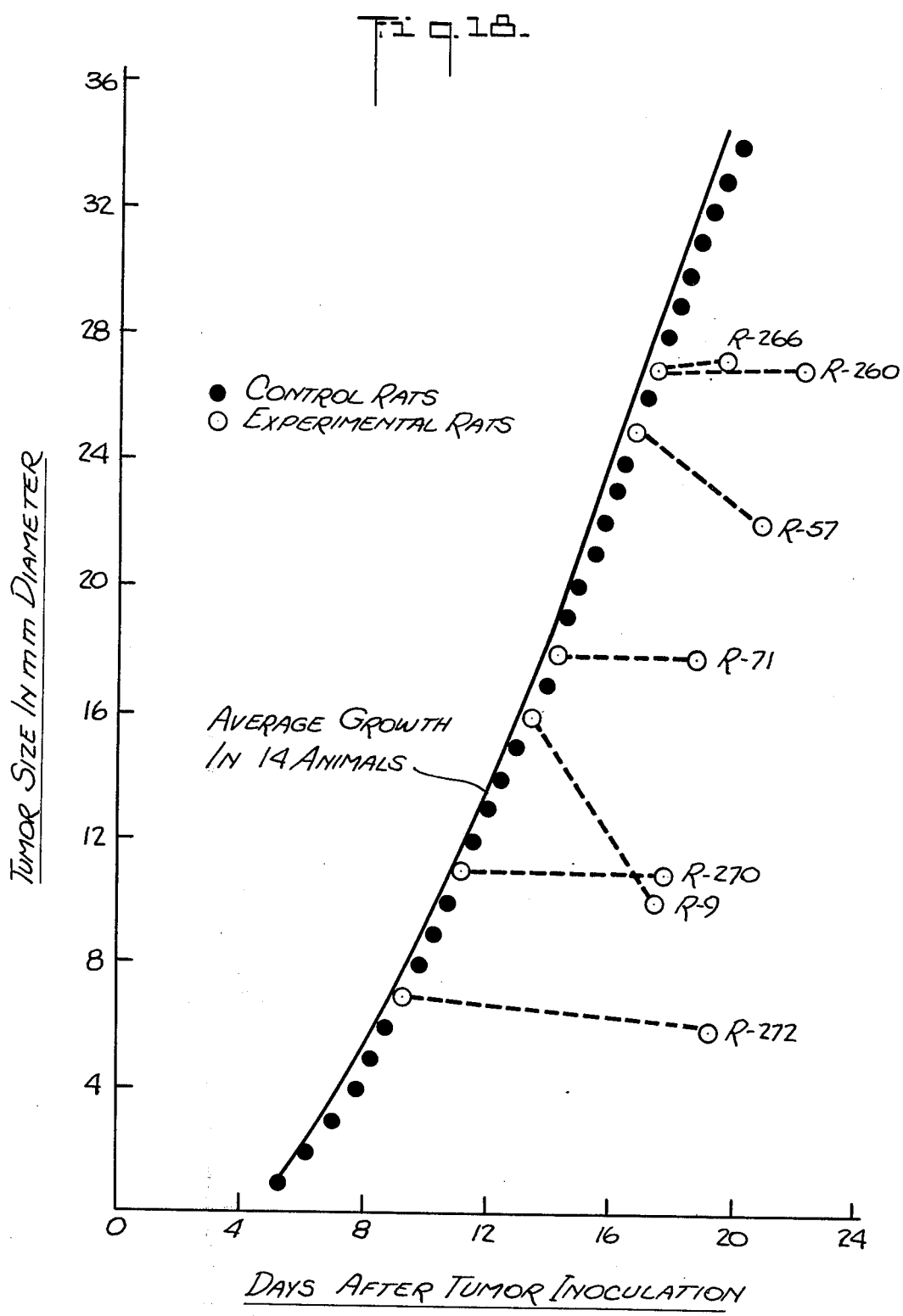

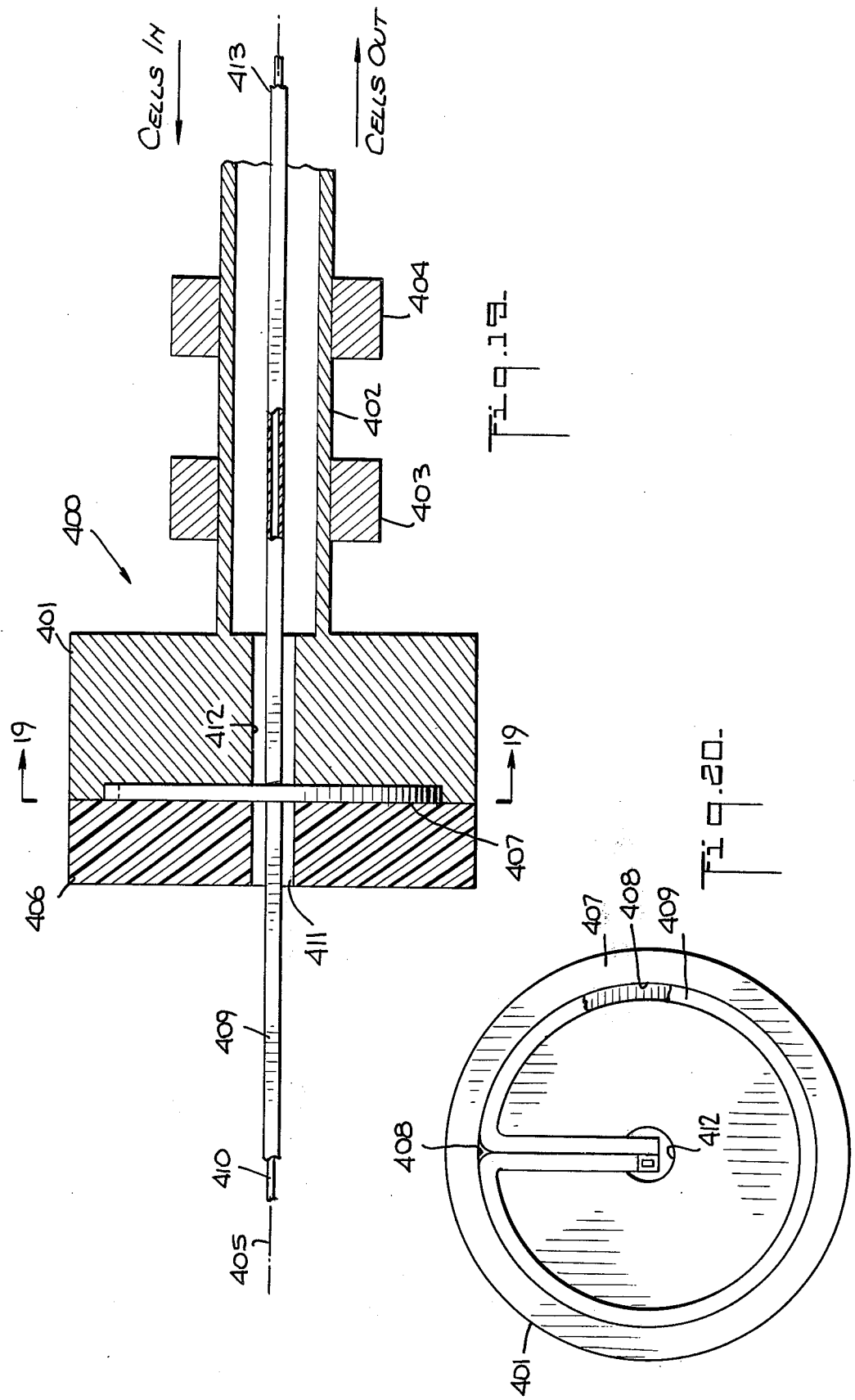

3,964,467

METHODS AND APPARATUS FOR AUGMENTATION OF THE PRODUCTION OF ANTI-BODIES IN ANIMALS AND HUMANS AND THE COLLECTION THEREOF

RELATED APPLICATIONS

The present application is a continuation-in-part of application Ser. No. 328,048, filed Jan. 30, 1973 which in turn is a division of application Ser. No. 136,476 filed Apr. 22, 1971, now U.S. Pat. No. 3,179,182. The subject matters therein disclosed are incorporated herein by reference, just as if fully set out herein.

BACKGROUND OF THE INVENTION

As disclosed in my above-identified applications, I have discovered that very large production of antibodies can be achieved by removing specific feedback regulatory antibodies by means of lymphoresis performed under special conditions in a patient or subject (e.g., an animal or human) with induced anatomical and physiological changes.

The subject is first given a specific antigen administration then, preferably, but not mandatorily, is splenectomized. A thoracic duct fistula is next performed. The central venous system pressure is then preferably raised so that it is above the atmospheric pressure of the thoracic duct. In this manner, substantially all the lymph fluid is allowed to flow out of the thoracic duct from the fistula (through an indwelling catheter) for a prolonged period of time. The lymph is separated into cells and lymph fluid, which latter contains the antibody produced in response to the specific antigen administered. The cells are returned to the subject intravenously. The subject must be given replacement fluid, which can be of several kinds, but all lacking the specific antibody.

In accordance with the present invention, a subject which contains the specific antigen is chosen, e.g., a patient with cancer or a subject already immunized, or making antibodies to an endogenous or exogenous antigen. The fluid which leaves the patient via the thoracic duct fistula cannula consists of lymph generated by the patient, and saline, which is continuously infused into the cannula to dilute the lymph. The lymph is actually the only fluid lost from the patient, inasmuch as saline, which is constantly infused into the cannula also leaves via the cannula. Furthermore, as set forth below in detail, in accordance with the instant invention, the patient's venous pressure is precisely controlled to assure that the patient's total lymph production egresses from the cannula, thereby achieving the most efficient augmentation of antibody production by the patient, and total loss by the patient of the antibody produced.

Because of this lack of antibody, in the presence of antigen administration, or antigen content, it is found that the antibody production in the lymphoid tissue, and therefore its content in the lymph fluid, is enormous and ever-increases. The tremendous increase in antibody production is several orders of magnitude greater than other modes of antibody production, and therefore has very substantial utility in the fields of biology, chemistry and veterinary and clinical medicine.

However, conventional apparatus used for performing the steps of the foregoing method is costly, inefficient, and inter alia tends to foster the generation of bacterial growth.

Accordingly I have invented apparatus having general utility in biochemical research, and particular applicability in the performance of my method for augmenting the production of antibodies.

Furthermore, my invention of this apparatus made possible novel improvements in my method for augmenting antibody production, and as well led to my discovery of novel methods for the treatment of cancer, for continuous mass in vitro suspension culture of mammalian and non-mammalian cells and to my discovery of novel methods for culture treatment in order to develop vaccines.

SUMMARY OF THE INVENTION

It is therefore an object of the invention to provide novel apparatus for performing my methods for augmenting the production of antibodies in animals and humans, and for collecting the antibodies thereby produced.

It is further object of the invention to provide novel apparatus having general utility in performing biochemical research.

It is still another object of the invention to provide improved and novel methods for augmenting antibody production in animals and humans, such methods having general utility in performing biochemical research in respect of the origin and control of diseases.

Still other and further objects of the invention are apparent to those skilled in the art from study of the within specifications.

In accordance with one aspect of my invention, a process for augmentation of production of a specific antibody from a patient comprises the step of administering a specific antigen to the patient to cause production of the specific antibody, or choosing a subject containing an antigen, e.g., cancer, or one already immunized or making antibodies to an endogenous or exogenous antigen. The process additionally includes the steps of performing a thoracic duct fistula, raising the patient's central venous pressure to eliminate alternate lymphatico venous channels, and collecting lymph from the fistula. The process further includes the steps of centrifuging the collected lymph to separate the lymph cells therein from the lymph field, and to form a thin elongated layer of the separated cells, treating the thin elongated layer of lymph cells to assure that they are substantially free of the specific antibody produced, and dispersing the cells in physiologically balanced saline solution. The process further includes the step of returning the dispersed cells and solution to the patient intravascularly, and giving appropriate replacement therapy intravascularly to the patient comprising fluid which can be of several kinds, but having in common that they are substantially free of said specific antibody to maintain normal control and health of all other systems in the body.

BRIEF DESCRIPTION OF DRAWINGS

FIG. 1 is a block diagram of a method for augmenting antibody production in accordance with the invention;

FIG. 2 is a plan section view of a centrifuge constructed in accordance with the invention, and used in performing the method diagrammed in FIG. 1, said section being taken along line A—A in FIG. 3;

FIG. 3 is a plan view of the centrifuge illustrated in FIG. 2, and including the power source therefor and connections thereto;

FIG. 4 is a schematic diagram of one embodiment of automatic pipetter 60 constructed in accordance with the invention, and used in performing the method diagrammed in FIG. 1;

FIG. 5 is a schematic diagram of another embodiment of the automatic pipetter 60;

FIG. 6 is a block diagram illustrating one mode of operation of the pipetter 60;

FIG. 7 is a block diagram illustrating the electrical interconnection of pipetter 60, motor controller 63 and venous pressure monitor 64;

FIG. 11 is a plan section view of a squeeze-type valve constructed in accordance with the invention and having utility in apparatus used for performing the procedure diagrammed in FIG. 1;

FIG. 12 is a simplified plan section view of a tube compression pump reservoir constructed in accordance with the invention and having utility in apparatus used for performing the procedure diagrammed in FIG. 1;

FIG. 13 is a top view of compression pump apparatus having utility in apparatus used for performing the procedure diagrammed in FIG. 1;

FIG. 14 is a plan section view of the pump apparatus illustrated in FIG. 13;

FIG. 15 is a plan section view of fluid handling and transfer apparatus constructed in accordance with the invention and having utility in apparatus used for performing the procedure diagrammed in FIG. 1;

FIGS. 17, 18 are graphs showing certain results of the procedure diagrammed in FIG. 1 performed on subjects treated for Murine Sarcoma Virus induced cancer.

FIG. 19 is a plan section view of another centrifuge constructed in accordance with the invention;

FIG. 20 is a front elevation view of the centrifuge shown in FIG. 19.

DETAILED DESCRIPTION OF EMBODIMENTS

Figure 8:
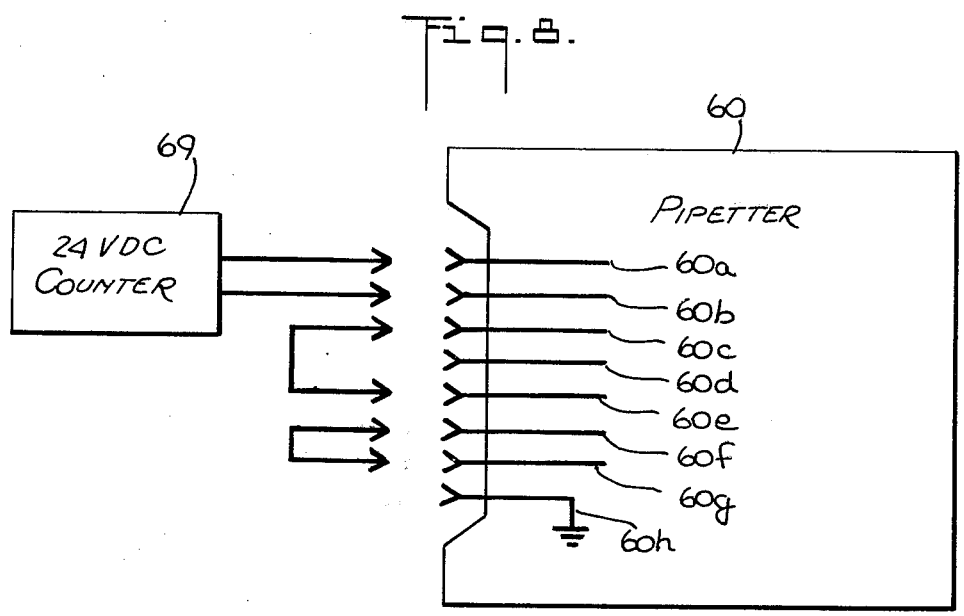
FIG. 8 is a block diagram illustrating another mode of operation of the pipetter 60.

My new and improved method for augmenting antibody production is shown in block-diagram form in FIG. 1. A subject 10 is treated with a specific antigen by the lymphoresis procedure disclosed in my above-identified applications. Alternatively, that procedure is applied to a subject containing an antigen e.g., cancer, or one already immunized or making antibodies to an endogenous or exogenous antigen. The lymph fluid thereby caused to flow at the outlet of a thoracic duct fistula 11, is processed in accordance with the instant invention. This depletion of lymph, which contains cells and lymph fluid, which latter includes specific antibodies generated in response to the applied or already contained specific antigen results in continued production of the specific antibodies, in tremendous quantities.

In accordance with the instant invention, the lymph fluid is taken from the subject 10 at the thoracic duct fistula, and is fed to a novel centrifuge 40 (FIG. 2), constructed in accordance with the instant invention. Operation of the centrifuge 40 separates the lymph cells, forming a thin layer of cells, from the lymph liquid containing the generated specific antibodies. This liquid and the antibodies therein are removed and fed to a stage for processing out the specific antibodies. The lymph cells, now free of lymph, and then dispersed and suspended in a solution, saline, and resulting suspension transferred to a reservoir 12 (for example, FIG. 12) or to a fluids handling and transfer apparatus (for example, FIG. 15), for returning the suspended cells into the vascular system of the subject. The patient is given replacement therapy which can be plasma not containing the specific antibody, which may contain cell free lymph liquid from an unimmunized donor or donors, or the subsequently processed lymph liquid of the subject, from which the generated specific antibodies have been removed, or the subsequently processed lymph fluid, from which various classes of macromolecules, which include the specific antibodies, have been removed.

The catheter preferably used in the fistula is made to have a double lumen. The larger lumen tube, through which the lymph flows, may have a polyethylene tip, which is attached to a silastic tube. The tip has a bevel for ease for entry, and a bump to insure that the ties behind the bump keep the catheter in position. The silastic tube which forms the main part of the catheter provides flexibility, so that small errors of alignment can be corrected without tension on the duct.

The smaller lumen tube is made from polyethylene and is "drawn out" in a stream of hot nitrogen to be of appropriate diameter for the particular patient being treated. The nitrogen treatment prevents oxidation of the surface of the polyethylene during the "drawing-out" procedure. The unaltered polyethylene surface thus retains its excellent anti-clotting property. The smaller tube, which is located inside the main tube, carries heparin in a saline solution to the very tip of the catheter. The saline solution may contain from about 4 to 100 units of heparin/ml and is infused up the catheter at a rate of from about 0.5 ml to 0.5 L. per hour, depending upon the size of the patient and the thoracic duct lymph flow rate. This prevents the lymph from clotting and reduces the chance of blocking of the catheter by cellular aggregates.

If the resulting fluid suspension is fed to the centrifuge in a manner described in detail below, via an automatic pipetter 60 (FIG. 4-9), the replacement fluid is thereby fed back to the subject, in a controlled manner, in response to signals coupled from a motor controller 63 and a venous pressure monitor 64, which monitors the venous pressure of the subject 10, at all times during the treatment.

Fluid which leaves the patient via the thoracic duct fistula cannula consists of lymph and saline. The lymph is the actual and only fluid lost from the patient. In accordance with the invention, the saline is added to the lymph fluid by constant and continuous infusion. The saline is pumped to the tip of the patient end of the thoracic duct catheter and is part of the incoming fluid which ensures a continuous washing of catheter, centrifuge and other associated on-line pieces of equipment, described in detail below. By increasing the venous pressure of the subject and by regulating the outflow resistance from the thoracic duct cannula so that the pressure in the thoracic duct is only a little, say 1–2 cm of water pressure, higher than atmospheric, the maximum differential between the venous and thoracic duct pressure can be established.

Such a differential ensures that the total lymph produced by the subject, and the total saline which is infused into the thoracic duct cannula, egresses from the cannula. Total egress of lymph is mandatory, per se, for the most efficient augmented antibody production, because it ensures total loss of newly synthesized antibody. In addition, total egress of lymph plus added saline is mandatory because it ensures that these two volumes can each be measured accurately. Accurate data of lymph loss per minute, per hour and per day are necessary to control the volume of fluid which must be replaced per unit of time to the subject losing lymph.

It is mandatory to maintain continuously the pressure in the thoracic duct at a pressure minimally above atmospheric despite changes in lymph flow, position of the subject and other factors which might alter such pressure. The maintenance of such a thoracic duct pressure is achieved in the following way, although other methods can be used to maximize the stability of such thoracic duct pressure under a wide variety of possible disturbing influences.

METHOD

A conventional differential pressure transducer is employed. Pressure from the thoracic duct is applied to one side of the transducer membrane and hydrostatic pressure from a liquid column originating at the height of the thoracic duct is applied to the opposite side of the transducer membrane. Using conventional electronic amplifiers and controls, the difference between the two pressures can be measured and will equal the thoracic duct pressure corrected for the elevation position of the subject with respect to the transducer. The hydrostatic pressure from a liquid column originating at the height of the thoracic duct is achieved by having a wide bore reservoir covered with an ultrathin nonelastic membrane or a porous membrane which allows free movement of air but not the liquid used in the manometer system. The wider the reservoir, with respect to the volume displacement required to operate the differential transducer, the more accurate is the correction for vertical position of the subject.

When both methods are used concurrently, the differential transducer should show that the "choker" method is operating successfully. However, under unusual circumstances, it may be necessary for the differential transducer to ring an alarm or control the thoracic duct pressure by one of two methods. For example, the input flow of saline up the thoracic duct could be altered by the transducer signal, thus altering the total thoracic duct cannula output flow, which in turn would be reflected by an altered pressure in the thoracic duct. Another method of regulating the pressure in the thoracic duct is to alter the level, with respect to the patient, of the liquid (outer fluid) which is displaced by the egressing lymph and saline (inner fluid).

In further accordance with the invention, fluid taken from the subject at the thoracic duct fistula 11 and fed to the centrifuge 40, and the replacement fluid fed back to the subject, is continuously monitored to assure that the subject is not depleted of vital fluids, and to assure that too much replacement fluid is not returned to the subject.

The basic structural details of my novel centrifugal separator, centrifuge 40, for separating the lymph cells from the lymph fluid, are shown in FIG. 2. Although conventional centrifugal separators can be utilized in performing my method, such conventional apparatus results in packing the lymph cells into a small pellet. As a result, it is difficult adequately to nourish all the cells in the pellet. Moreover, large amounts of force are necessary to disperse these cells into a suspension suitable for restoring them intravenously to the subject 10 being treated.

My centrifuge 40, however, separates the cells in such a thin layer that virtually all receive normal nourishment from the lymph which is flowing past them. For antibody production and for cancer therapy, it is extremely important that the cells contained in the lymph fluid be returned to the subject with minimal or no damage. Normal nourishment of the cells during their extra corporeal circulation greatly minimizes damage to the cells.

Furthermore, when the cells are centrifuged into a thin layer, rather than into a pellet or thick layer, less shearing force is required to disperse them, and this again minimizes cell damage. Centrifugation of the cells into a thin layer is not achieved in conventional centrifuges, but is achieved in the present centrifuge 40 because of the large surface area of the inner surface 41 of the outer wall 42 of the centrifuge bowl or shell 45, which entire surface is also equidistant from the center of rotation 43.

A centrifugal separator 40 (FIG. 2) constructed in accordance with the invention comprises an annular member or core 44 secured by bolts 47 (only one shown) to a shell member 45, and to end cap member 46, which is seated in a stepped recess provided therefor in the base of core 44. Hub 48, from which the shaft 49 extends, is secured to end cap 46 by bolts 47' (only one shown).

The shaft 49 is journaled in supported bearing blocks 50 (FIG. 3). An electromagnetic brake 51 and a pulley 52 are mounted on the distal end of the shaft 49. A belt 53 (illustrated in phantom) couples pulley 54, driven by motor 55, to pulley 52 to rotate shaft 49 about axis 43 (FIG. 2).

Materials to be separated are admitted to the centrifuge 40 through polytetrafluoroethylene tubing 56a which is secured to shell member 45 by button 45a of the same material (FIG. 2). Tubing 56a opens into the annular chamber 40a defined by the walls of core member 44 and the inner wall 41 of shell member 45; the annular chamber 40a comprises the centrifuge chamber. An O-ring 44c provides a seal for this chamber.

Radial bores 44a formed in the base end of core 44 open into the centrifuge chamber 40a. The distal ends 44b of bores 44a open into polytetrafluoroethylene tubing 56b, which is secured to the core 44 by means of a force fit inside a shaft 56c of the same material. Intermediately located polytetrafluoroethylene guide members 57 (FIG. 3) support the ends of tubing 56a, 56b which are connected respectively to conventional rotating seals 58a, 58b.

In operation, lymph, including lymph cells and lymph fluid removed from the thoracic duct fistula 11, is fed at a defined rate from the reservoir 12 (FIG. 12) or the fluids handling and transfer apparatus (FIG. 15) into the centrifugal separator 40 through inlet port 59a (FIG. 3). The bowl is rotated around its axis 43 at a speed large enough to exert a high enough gravitational force on the lymph cells to move them across the centrifuge chamber 40a to the inner wall 41 of the centrifuge shell 45, where they form a thin layer over the surface of wall 41. Formation of a thin layer of cells is achieved by controlling the number of cells, which enter the centrifuge, and the surface area of the inner wall 41. Formation of a thin cell layer is greatly assisted by controlling the rate at which lymph is fed into the centrifuge with respect to the gravitational force generated by the centrifuge.

After a preselected period of time, and while the bowl is rotating, the cell-free lymph fluid is removed at outlet port 59b (FIG. 3), a saline solution for example, is introduced at the inlet portion 59a. In order to further treat the lymph cells to remove antibodies, this solution may contain additional chemicals, known in the art.

The centrifuge is then braked by electronmagnetic brake 51, to disperse the lymph cells, which had been collected in a thin layer on inner wall 41, into the added solution. The centrifuge is again operated to separate the cells from the added solution, which then can be removed to allow addition of further saline. The centrifuge is again braked to disperse the collected lymph cells in the solution. The dispersion formed is removed from the centrifuge. The subject is given replacement therapy, intravascularly, which can be lymph fluid which is free of specific antibody. This fluid can be obtained from one or more donors, or may comprise the subject's lymph fluid, which has been treated to remove the specific antibodies, or that class of macromolecules which include the specific antibodies.

AUGMENTED PRODUCTION OR MACROMOLECULES

The same principle and general procedure can be applied to the collection of the augmented production of molecules other than antibodies. The circulating level of most molecules in the body is regulated in such a manner that a constant blood or extra-cellular level of that molecule is achieved. If the subject is depleted of a particular molecule, and more especially if that depletion occurs prior to the molecule reaching the blood stream, the body senses the depletion through various mechanisms and initiates and maintains increased production in an attempt to correct the specific depletion. If the depletion is maintained despite increased production there will be an ever increasing production of the specific molecule until the limit of production capacity for that molecule is reached.

Molecules produced and secreted by cells of the body, having a molecular weight greater than 100,000, enter the lymphatic capillaries preferentially to the capillaries of the blood circulation. The reason for this preferential movement lies in the fact that there are actual spaces between the cells making up the wall of the lymphatic capillaries. There are no spaces between the cells making up the wall of the blood capillaries and furthermore there is a continuous basement membrane on which the cells lie. Thus the molecules of large molecular weight can enter directly into the lymphatics through these inter-cellular spaces and they do so preferentially and almost quantitatively compared to their entering the capillary circulation, by diffusion which is the only mode available into this circulation. The result of this preferential movement of large molecules is that virtually all newly synthesized large molecules enter the thoracic duct (of animals or subjects with raised venous pressure) and can thus be eliminated prior to their entering the blood stream. This elimination leads to an increasing production of that molecule which can thus be collected in large amounts. Molecules belonging to the above class may include tumor antigens, various components of complement (necessary for certain immunological reactions), anti-haemophilic factors, anti-emphysemia factors, hormones and other compounds.

CANCER TREATMENT

The nature of the interaction between the immune system and the tumor can be described as a relationship between a highly feedback controlled immune system and an uncontrolled proliferation of tumor cells. Such a relationship is basically unstable and leads to an ever increasing disparity between the level of specific immune action and the size of the tumor mass. Moreover, this disparity seems to result in favor of continued tumor growth even when the tumor is extremely small, that is, or a size which is not even clinically recognizable.

On the other hand, it is known that the immune system has an enormous potential for augmentation, which potential augmentation can be estimated to be in the region of millions to billions.

The same theory and practice of removing feedback antibody as is applied to augmentation of antibody production, can be applied to augment the immune response against cancer.

However, the immune response to cancer is rather more complex than the immune response to simple antigens and bacteria. With respect to cancer, it seems that some components, namely immunoglobulins of the class termed IgG, which are themselves not cytotoxic to cancer, act as specific feedback mechanisms to prevent the production and action of other components such as IgM and sensitized lymphocytes, which are cytotoxic to cancer cells. The same basic procedure which is used for augmented antibody production can be used to augment the immune response against cancer, and at the same time can be used to retain (by returning to the blood circulation) those components which are cytotoxic to cancer cells, and eliminate those components which block the production and action of the cytotoxic components.

The separation of the antibody into cytotoxic and non-cytotoxic blocking and feedback antibodies may be achieved by ultra-centrifugation or precipitation methods and other techniques, because the cytotoxic components have a different molecular weight and other properties. It is presently not known whether or not any of the subclasses of smaller molecular weight antibodies of the IgG class should also be returned to the subject during the above procedure, but as is discussed subsequently, such antibodies can be used in other ways.

However, even non-cytotoxic antibodies can be made effectively cytotoxic by attaching them to radioactive compounds, cytotoxic drugs or to agents such as haptene or foreign proteins, e.g., sheep IgG, to which the subject has been sensitized. Before pursuing this latter line of reasoning it must be noted that there is another reason apart from feedback control of the immune state which causes the immune system to fail in its fight against cancer. This second reason is due to the fact that cells shed their surface membranes into the extra-cellular body fluids. This is known for lymphocytes (Nossal), other normal cells (Pressman) and tumor cells (Baldwin and Hellstrom). The continuous release of tumor antigen by cancer cells can complex every immune component which is specifically directed against the cancer, and this complexing can render all such components ineffective.

Furthermore, it is known that excess and continuous antigen dose, especially of weak antigen, causes specific paralysis of the immune system to that particular antigen. A similar phenomena is almost certainly operating in a subject with cancer.

My described method of fistula procedure in subjects with raised venous pressure will eliminate virtually all such newly synthesized, released and circulating antigens, because they are generally of high molecular weight. Eliminating excess released and circulating tumor antigen will prevent active immune components which have been generated against cancer from becoming inactive.

In one series of successful tests of my method for augmenting immunity against cancer, adult male BN rats weighing 200-250 grams, and obtained from Microbiological Associates, Bethesda, Maryland, were used.

A tumor was induced by inoculation of Murine Sarcoma Virus (M.S.V.) into neonatally thymectomized rats. This tumor is transplantable and possesses a tumor specific transplantation antigen as demonstrated by transplantation resistance. The tumor regularly kills recipients if they are given an appropriate dose of tumor cells, for example, $0.5 \times 10^6$ animal passaged cells or $0.1 \times 10^6$ cultured tumor cells. The tumor was carried in tissue culture and in BN animals by serial transfers when the tumor reached a diameter of approximately 1½-2 cm.

Experiments with animal passaged cells were carried out after subcutaneous inoculation of $0.5 \times 10^6$ viable tumor cells as determined by trypan blue dye exclusion.

Figure 17:
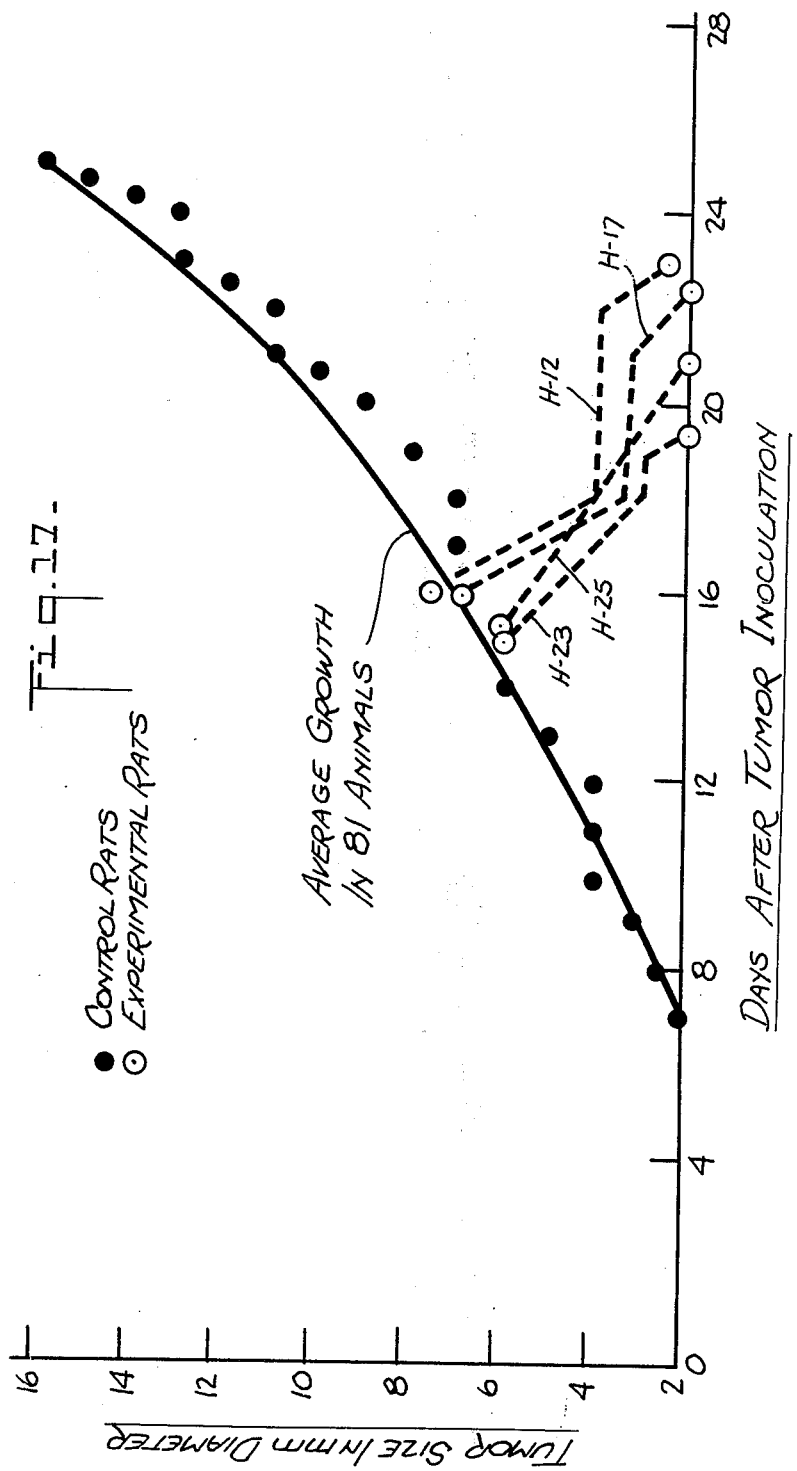

Experiments with cultured tumor cells were carried out after subcutaneous inoculation of $0.1 \times 10^6$ tumor cells. number The fistula procedure and replacement therapy described above were followed in respect of these animals. FIG. 17 illustrates tumor growth after subcutaneous inoculation of $0.5 \times 10^6$ animal passaged Murine Sarcoma Virus induced tumor cells in control (curve shows average growth in 14 animals) and individual experimental BN rats. The 14 control rats were subjected to the thoracic duct fistula procedure and the lymph fluid and cells were returned intravenously. The cells in the lymph, but not the lymph fluid, were returned to the experimental rats. The lag period before appearance of the tumor and the growth rate of the tumor are shown in FIG. 17. In four animals (H-12, H-17, H-23 and H-25) the entire procedure was technically successful. On the second day of fistula procedure the tumors became less firm and then completely regressed on Days 4-7 (FIG. 17).

Furthermore, FIG. 19 illustrates tumor growth after subcutaneous inoculation of $0.5 \times 10^6$ tissue cultured Murine Sarcoma Virus induced tumor cells in control (curve shows average growth in up to 81 animals) and individual experimental BN rats. The experimental animals were subjected to the fistula procedure, the cells contained in the lymph fluid were returned intravenously and the lymph fluid was wasted. The lag period and growth rate of these tumors are shown in FIG. 18. The tumors of all experimental animals undergoing a technically "successful" procedure showed marked tumor regression (FIG. 18). At autopsy after sacrifice of these rats, the tumors appeared haemorrhagic and necrotic.

After inoculation of "animal passaged tumor cells" into control animals, the tumor growth was slower than the tumors derived from cultured cells. My fistula procedure produced a more dramatic regression of tumors derived from animal passaged cells as compared to tumors derived from cultured cells. The explanation for these differences is not known. However, when animal passaged cells were transferred, a considerable under of "immune" cells of various kinds may also have been transferred and thus account for the above phenomenon.

In any event, the use of my fistula procedure caused regression of M.S.V. induced tumors growing in syngeneic rats.

Returning to the question of converting noncytotoxic antibodies into ones which will kill tumor cells, the process of killing cancer cells by "converted antibodies" can be readily demonstrated in tissue culture, because there are no interfering compounds, namely free tumor antigen, which could interact with the converted antibodies and make them ineffective. Moreover, there are no natural specific antibodies against the cancer present in tissue culture, and thus all the available antigenic sites are available to the converted antibody.

The situation in tissue culture is completely different to that found in the body of a subject with cancer. In this latter situation circulating free tumor antigen is present, and complexes the converted antibody. In addition, circulating anticancer antibody, which is continuously generated by the subject, can dilute the "converted antibody" to such an extent that there is very little localization of the "converted antibody" in the tumor.

My thoracic duct fistula procedure, which eliminates all newly synthesized circulating tumor antigen and antibody, allows the "converted antibody" to act in the same way as it does in-vitro tissue culture. A special case is where the subject (say a human) is sensitized to say sheep IgG. Sheet anti-"human tumor antigen" antibody is prepared. At the present state of the art this antibody cannot be prepared in a pure form, thus restricting its value. But my fistula procedure decreases the severity of this restriction.

Alternatively, all the IgG including anti-tumor antibodies of the IgG class, which are generated and collected by the cancer patient on fistula procedure, are bound to sheep IgG in the region of anti-tumor antibody excess. These "complexes" will be directed to antigens which are foreign to the healthy subject, and this will include the subject's tumor antigen. Again, the fact that the "complexes" are not directed solely to tumor antigen, restricts their value, and again my fistula procedure decreases the severity of the restriction. Antibodies generated in one subject and treated by the above method may be used successfully to treat other subjects with a similar kind of cancer.

My fistula procedure which quickly eliminates interfering newly synthesized circulating tumor antigen and antibody, will also be used to eliminate sheep IgG, which is not firmly attached to cells with a high binding affinity. That is, my procedure will eliminate circulating and non-specific bound sheep IgG, which binding has a low affinity, and can thus be removed by lowering the concentration of sheep IgG in the extracellular fluid. The elimination of sheep IgG, which is not bound to cancer cells, will largely limit the natural and cytotoxic hypersensitivity (because the subject is sensitive to sheep IgG) reaction to all but cancer cells.

In brief review, it is seen from the above description of my immunological methods in respect of cancer, that all the procedures involve my fistula method for augmenting antibody production. In respect of the rats to which my fistula procedure was applied, as described above with reference to FIGS. 18, 19 the lymph cells were returned to the patient after being washed with a physiologically balanced saline solution, e.g., Ringers solution.

I believe that this immunological method caused remission of the cancer in these rats for the following reasons. It is known that addition of antibody to a patient decreases the patient's production of cell mediated immune (CMI) cells. By application of my fistula procedure, antibody production is augmented, and the antibodies removed from the patient. Thus, it is believed that CMI cell production is augmented. Furthermore, washing of the lymphocytes before returning them to the patient removes tumor antigen from the lymphocyte receptors, thereby unblocking the CMI cells.

It should be noted that the lymphocytes can be treated for various purposes, while they are outside the patient's body, in a manner that cannot be effectively done while they are in the body. Thus, for example, the lymphocytes can be treated with drugs or special compounds, for example, enzymes such as trypsin and neuraminidase, which have been added to the washing solution, or coated along the centrifuge wall 41. Similarly, the body of the patient can be treated in various ways while the lymphocytes are outside, in manners that cannot be effectively done while the lymphocytes are in the body. For example, conventional drugs for slowing down the activity of cancer cell membranes to retard shedding of tumor antigens also slow down lymphocyte activity, an undesired result. Such drugs can be administered to the patient undergoing my fistula procedure before his lymphocytes are returned. This drug has the desired effect on the cancer cells and no effect on the lymphocytes.

In addition to returning the lymphocytes after washing, antibodies produced by the patient can also be returned. As shown in my patent, production of IgM antibody in a stabilized immunosystem exhibits a peak, and then falls to zero, at about the same time that IgG production reaches a plateau. Use of my antibody augmentation method results inter alia, in renewal in large amounts of IgM antibody production. Since no IgG antibody is returned to the patient, the IgM production continues. Moreover, IgM antibody, which is cytotoxic to cancer, exhibits no feedback effect. Accordingly, if separated from the IgG antibody, washed, and returned to the patient with the lymphocytes an enhanced attack on and destruction of the tumor cells is expected.

Furthermore, it is noted that use of my fistula procedure removes free tumor antigens from the patient. It is known that low levels of IgG antibody blocks the action of lymphocytes in the presence of tumor antigens. Accordingly, if the separated augmented IgG antibody produced by my method is collected and returned to the patient after washing, along with the lymphocytes an enhanced attack on and destruction of the tumor cells is expected.

In addition, the IgG class of antibodies produced by my fistula procedure, can be made radioactive before returning them to the patient. Although only a small portion of the IgG antibody is specific to the cancer in the patient, high levels of radiation are not produced in the patient, since the non-specific-to-cancer IgG antibody given back to the patient simply passes out the thoracic duct fistula along with unattached tumor antigen, while the radioactive specific-to-cancer IgG antibody attaches itself to tumor antigen attached to the tumor cell membrane, thereby enhancing the attack on and destruction of the cancer cells. It should be noted that the collected IgG treated or not can be expected to have the same effect when administered to other patients having the same cancer.

Instead of, or in addition to the radioactive treatment of IgG antibody, these antibodies can be attached to compounds such as protein or haptene to which the patient has been sensitized. Then, the attached compounds are returned to the patient, whose lymphocytes are still outside the body. The specific-to-cancer antibody combines with tumor antigen attached to the cancer cell membrane. The non-specific-to-cancer antibody is eliminated at the thoracic duct fistula. Then, the lymphocytes are returned to the presensitized patient and react violently with the compound to which the specific-to-cancer antibody is attached, the expected result being destruction of the tumor cell as well. It should be noted that, to prevent the patient's premature reaction to the compound to which he has been sensitized, complement containing replacement therapy, for example, plasma, is not given to the patient, but rather non-complement containing therapy, such as albumin is. Then, when the lymphocytes are returned, plasma therapy is also restored, to allow reaction of complement with the antibody carrier compound.

Next, my fistula procedure can be used to make heterologous antibody in sheep, for example. My fistula procedure for augmenting antibody production is performed on a sheep inoculated with cancer cells from a patient to obtain large amounts of antibody which has an IgG component specific to the cancer. This antibody can then be mixed with normal cell tissues of the cancer patient to eliminate as much of the other IgG components as possible. The resulting antibody, which contains an IgG component specific to the cancer in question can then be administered to the cancer patient who is also on my fistula procedure, in the methods just described, the expected result being an enhanced attack upon and destruction of the tumor cells.

APPARATUS USED IN PERFORMING ANTIBODY AUGMENTATION PROCEDURE

Although biomedical apparatus of conventional construction can be used to perform my novel method for augmenting antibody production, I have invented novel apparatus for effecting this procedure.

In one apparatus embodiment of my method for augmenting antibody production shown in FIG. 1, a tube compression pump reservoir 12 made of thin-walled silicone rubber, is employed (FIG. 12). An outer housing 14 thereof is made of rigid polycarbonate or other materials which are autoclavable, although lucite or other plastics may be used if desired. Saline (outer fluid) is pumped by pump 13 of conventional construction, or as illustrated in FIGS. 13, 14, through inlet pipes 15, 16, while outlet pipes 17, 18 are closed by valves (not illustrated), around the silicone rubber bag 12 to expel the contents thereof into the subject.

Furthermore, an exact measurement of how much fluid has been taken from the subject can be made when this pumping system is used, by measuring the amount of saline displaced by the lymph or the amount of saline necessary to evacuate the silicone rubber bag 12. Solenoid valve blades 19, 20 (FIG. 12) are actuated directly by signals from the photoelectric cells of the automatic pipetter to occlude the flow from centrifuge 40 and open the connection to pipetter 60, respectively, during this operation. Thus, the pumping system is quite separate from the fluid which is being administered to the subject. It is this means in this embodiment which allows for sterility, absence of air, possible refrigeration, and lack of necessity of having electronic equipment near the subject.

Although pumps of conventional construction can be used, I prefer to construct pump 13 as illustrated in FIGS. 13, 14. In this embodiment, a motor 200 drives a chained pair of piston-type pumps 201, 202. Piston driving screws 203, is driven by a chain 205 and sprockets 206, 207. Sprocket 207 is driven by chain 208 and sprockets 209, 210 which are driven by motor 200.

The pump cylinders and driving screws are mounted on supporting plate 211. Driving screws 203, 204 are at one end secured to torque plates 212, 213 respectively. Rotation of screws 203, 204 produces longitudinal movement of pump pistons 214, 215 respectively, causing contraction and expansion of pump chambers 216, 217 respectively, since screws 203, 204 are threaded in opposite directions.

Pump chambers 216, 217 are of equal volume, and have outlets 218, 219 respectively, and are sealed at their respective opposite ends by plastic membranes 220, 221. Limited switches 222, 223 control the direction of rotation of motor shaft 224, thereby controlling the extent of travel of pistons 214, 215.

In accordance with another aspect of the invention above-described with reference to FIG. 1, fluids handling and transfer apparatus is provided and includes an automatic pipetter 60, illustrated in FIGS. 4 to 9. Referring first to FIG. 4, this apparatus includes a vertically oriented, calibrated pipette 70, and a pair of optoelectronic devices 71, 72, for which can be photosensitive controllers, for example, photocells, which detect the upper and lower levels 73, 74 or fluid in the pipette 70.

In operation, the pipetter 60 apparatus accepts an electrical control signal from motor controller 63 (FIG. 1) to initiate discharge of fluid from pipetter outlet 75 (FIG. 4). When the fluid level in pipette 70 falls to the lower level 74, photosensitive controller 72 activates the appropriate valve combination to terminate discharge of fluid from pipetter outlet 75. Fluid input at pipetter inlet 76 continues, until the fluid in pipette 70 reaches upper level 73; at that time, photosensitive controller 71 acts to terminate the fluid input at inlet 76. The pipetter 60 is then again ready to discharge a predetermined amount of fluid to the subject in response to a subsequently occurring control signal.

Electrically controlled valve solenoids of conventional construction (not illustrated), having valve blades 77, 78, 79, 80, 81, regulate the flow of fluid between pipetter inlet 76 and outlet 75. In particular, in the quiescent state of the pipetter 60, valve blades 77, 79, 81 are occluding and valve blades 78, and 80 are open. When fluid is being accepted from the pipetter inlet 76, valve blades 78, 79, 81 are occluding and valve blades 77 and 80 are open. When pipette 70 is being discharged through the pipetter outlet 75, valve blades 77 and 80 are occluding, and valve blades 78, 79, 81 are open.

Referring to FIG. 6, one mode of operation of the pipetter 60 is illustrated. In this arrangement, the pipetter 60 discharges a predetermined quantity of fluid each time the output switch 61 of a conventional timer 62 is closed. In respect of the electrical input terminals of the pipetter 60, d-c power, for example, 24 volts, is coupled to terminal $60a$. Terminal $60b$ is a counter output terminal, which can be connected to an external counter to record how many times a predetermined quality of fluid is discharged from the pipetter 60. In a preferred pipetter embodiment, the voltage at this terminal falls from the power supply level to about zero volts, for a short period of time, for example, about 0.08 seconds, each time the fluid level in pipette 70 falls below the lower level 74.

Furthermore, terminal $60c$ provides a voltage output having first and second states representative of certain fluid levels in pipette 70. The first state obtains when that level is below level 73; the second state obtains when the level is at, or higher than level 73. Terminal $60d$ provides a voltage output having third and fourth states representative of other fluid levels in pipette 70. The third state obtains when that fluid level is at, or higher than level 74; the fourth state obtains when that fluid level falls below level 74. In the preferred embodiment, the first and third output states, and the second and fourth output states have the same voltage.

Terminal $60g$ is the command inhibit input terminal; terminal $60e$ is the discharge command input terminal. When terminal $60g$ is an open circuit condition, the pipetter 60 ignores any signal supplied to terminal $60e$. When terminal $60g$ is electrically coupled to the common ground, terminal $60f$, directly or through a resistance of 10 ohms or less, a command input signal at terminal $60e$ is effective to initiate discharge of a predetermined quality of fluid from the pipetter 60. Lastly, terminal $60h$ is a chassis ground for minimizing electrical shock hazards.

In accordance with the invention, FIG. 7 shows a typical system interconnection of the apparatus of FIG. 1. A motor controller 63 is constructed and arranged to develop power and control signals to actuate the pipetter 60 and pump 13. A venous pressure monitor 64 is constructed and arranged to provide a command inhibit signal from its terminal $64c$ to the motor controller 63, whenever the venous pressure of the subject being treated increases above a preselected level, thereby preventing discharge of fluid from the pipetter 60 into the subject, when the fluid in pipette 70 reaches level 73.

Moreover, monitor 64 is so constructed and arranged that whenever the venous pressure of the subject being treated reaches a critical predetermined level, monitor 64 switch 65 is actuated to turn on alarm lamp 66. In an alternative arrangement, the lamp 66 can be omitted, and the electrical interconnections of the venous pressure monitor 64 terminals can be modified, so that when the venous pressure of the subject being treated reaches that critical level, terminals $64a$ and $64f$ open circuit, and terminals $64a$ and $64d$ short circuit, to provide a suitable, audible or visual alarm indication.

With reference to FIG. 7, the system components are electrically interconnected by cables 67, 68. When the fluid level in pipette 70 reaches level 73, the signal produced at terminal 60c is coupled to the start terminal 63b of motor controller 63, and results in turning on pump 82 (FIG. 4), and the peristaltic or tube compression pump 13 apparatus, which supplies fluid from the reservoir 12 to the pipetter inlet 76. At the same time, the motor controller 63 generates a signal, which is coupled from its terminal 63d to pipetter terminal 60e to activate the valve solenoids, opening and closing the appropriate valve blades 77–81 to discharge fluid from the pipetter outlet 75. When the fluid level in pipette 70 falls to level 74, the appropriate valve blades are closed to terminate the discharge, and to allow pipette 70 to be refilled. Then, a signal is coupled from pipetter terminal 60d to motor controller terminal 63c, which thereupon turns off the pump motors.

In another embodiment of the system illustrated in FIG. 7, an appropriate timer can be electrically inserted in the lead coupling pipetter terminal 60c to the motor controller start terminal 63b to provide predetermined timing of the pipetter 60 operation.

FIG. 8 shows another mode of operation of the pipetter 60, which results in a self-actuating circuit for controlling the discharge of pipetter 60, and for measuring the discharge thereof by a conventional counter 69. This circuit interconnection can be used with the pipetter embodiment shown in detail in FIG. 5.

In the FIG. 5 pipetter embodiment, fluid fed into pipetter inlet 76 flows continuously into the storage stand pipe 83. Unless fluid also covers the top photocell 71 aperture, the pipetter 60 inlet valve blade 77 is open, letting fluid from the stand pipe 83 enter the pipette 70. When the fluid level rises to the upper level 73, the signal from terminal 60c starts the pump 82 motor and sets the pipetter 60 valve blades to drain, if the wiring arrangement of FIG. 7 is used. If the FIG. 8 wiring arrangement is used, the pump 82 runs continuously, and the command signal at pipetter terminal 60c is used directly as the pipetter 60 discharge signal, and so is coupled into pipetter terminal 60e.

While fluid discharge is occurring from pipetter outlet 75, fluid continues to flow into the stand pipe 83. Discharge from outlet 75 terminates when fluid in the pipette 70 falls below the lower level 74. The control signal thereby generated resets the appropriate valve blades to prevent further discharge from pipetter outlet 75, and, in the case of the FIG. 7 wiring arrangement, turns off and brakes the pump 82 motor. The inlet valve blade 77 immediately reopens, since the fluid level is below level 74, and the pipette 70 is refilled from the stand pipe 83.

As shown in FIG. 8, the counter 69 registers each occurrence of fluid falling below the lower level 74. Thus, in a given time, the counter 69 registers a number of pipettes (70) full of fluid which have been delivered to the subject. The total fluid quantity passed from pipetter outlet 75 is the counter number times the pipette 70 volume includes between the two levels 73, 74. The average rate of fluid flow for the period is this fluid quantity divided by the time during which the counter is recording.

Figure 9:
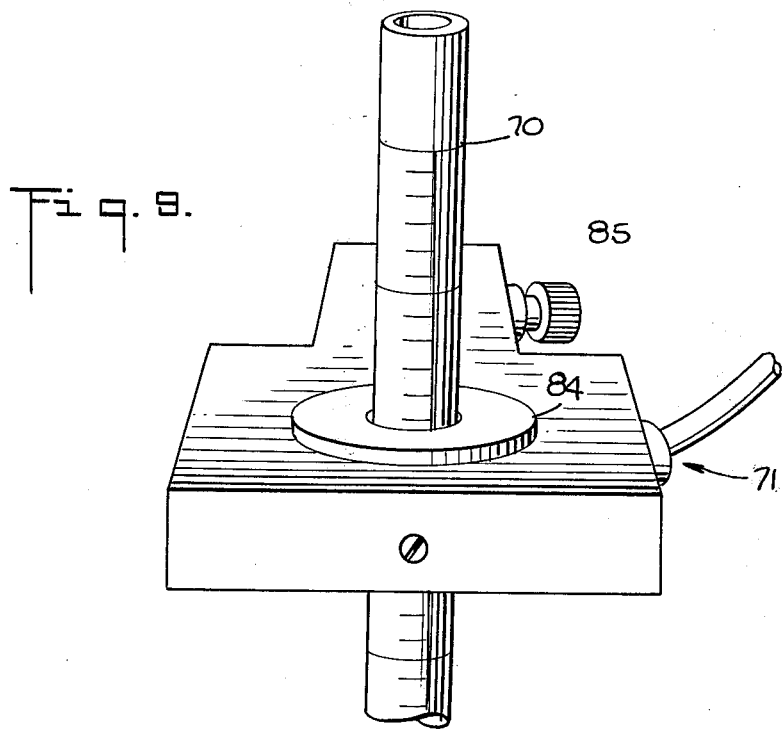
FIG. 9 is a perspective view of a portion of the apparatus incorporated in pipetter 60.

Referring to FIG. 9, in the preferred embodiment of pipetter 60, the pipette 70 is placed through the photo cell 71, 72 heads in such manner that each head covers a full diameter of the pipette 70. It is preferable to rotate the pipette 70 so that its calibration and other marks are toward the rear, since calibration marks on the pipette 70 somewhat obscure the photo cell 71, 72, if they fall in the front light path. It should be noted that the measuring position in each photo cell 71, 72 head is half way up the axis of the central optical insert 84. However, since a delivered volume setting is usually made, one need set only the difference between the two photo cell head positions. This is most easily done by aligning the top surface of the central optical insert 84 against the desired pipette 70 calibration marks, and then tightening the position clamping screws 85.

In one preferred pipetter 60 embodiment, tubing sections 86 to 91 are made of elastomeric tubing no stiffer or harder than TYGON (Registered trademark), having a 3/32 inch inner and 5/32 inch outer diameters, or silicone rubber having 1/16 inch inner and 5/32 inch outer diameters.

In summary, when the pipetter 60 is used in conjunction with a tube compression or peristaltic pump 13, and a conventional timer, the pipetter 60 delivers a fixed (but controlled) number of packages of fluid per day. The volume of each fluid package is controlled, and is the volume of fluid contained in the pipette 70, between two photo cells 71, 72. The pipetter 60 functions with a pump 82, which can be operated continuously. In this arrangement, solenoid valves open and close the valve blades 77–81 in such a manner that the continuously operating pump 82 circulates fluid round and round a circle, until an electrical control signal changes the configuration of the valve blades, so that the pump 82 now delivers the volume contained in the pipette 70 between the levels 73, 74 to the subject.

In another embodiment, the pump 82 only operates when a package of liquid is being delivered. In order to gain accuracy in both systems, the solenoids operate in such fashion that if one portion of the tubing sections 86–94 is pinched, another portion is released, so that the internal volume of the tubing system remains constant. In addition, in the second embodiment, an electronically controlled motor brake is provided so that the pump 82 does not have an overrun when it is switched off.

In summary then, the automatic pipetter 60 enables the investigator to deliver to the subject a variable number of packages of liquid per day. In addition, the volume of these packages can be controlled. In this way, the total volume of fluid delivered can be accurately regulated. The total volume of fluid delivered can also be measured by the volume of fluid which has been depleted from the reservoir 12 feeding this apparatus. Alternatively, the amount of fluid delivered can be estimated by the number of packages multiplied by the volume of each package. The advantages of the reservoir 12 and its outer housing 14 can be appreciated by the fluid logic of this administration system, which makes for ease of sterility.

Furthermore, the automatic pipetter 60 can function in such a way that the volume of fluid administered to the subject is an exact function of the amount of fluid which the subject loses by way of lymph collected. The lymph lost by the subject does not have to move up the pipette 70. Instead, the lymph fluid is separated from the measuring fluid by a lymph transfer chamber. This can be a small polished polycarbonate housing made of two halves, which clamp a very thin silicone rubber sheet. As the lymph enters this unit, it displaces the fluid, for example, water, up the pipette 70 through the thin silicone diaphragm. Such action triggers the operation of pipetter 60.

A third method of using the automatic pipetter 60 is to give fluid by a series of packages until a certain physiological parameter has been reached. For example, an important step of my method of augmenting antibody production, is to increase the venous pressure of the subject to eliminate alternate lymphatico venous channels. This can be achieved by surgical techniques and/or by giving serum proteins, which increase the osmotic pressure of the blood and so increase the venous pressure. I have discovered that, although it is necessary to raise the venous pressure to a high level to eliminate the alternate lymphatico venous channels, it is not necessary to hold the venous pressure at that high level, for example 15 cms. water pressure, which can be dangerous to the health of the subject. I have discovered that the venous pressure can be lowered to a safer raised level, for example, 6 cms. water pressure, to keep the alternate lymphatico venous channels eliminated. Furthermore, I have discovered that these channels can also be kept eliminated by intermittently raising and lowering the venous pressure between these raised levels, while the lymphoresis process of my invention is being given, with the same beneficial result, i.e., less stress on the subject.

Moreover, I have discovered that, in order to achieve and/or maintain a stable increased venous pressure without killing the subject, it is necessary that the venous pressure is measured prior to giving each fluid package. If the venous pressure is above the required level, that package is not given. If the venous pressure is below the required level, that package is given. Since the decision to give a fluid package, or not, is made 100 to 1000 times per day, it can be seen that this method enables one to give serum up to the development of a certain venous pressure.

A fourth method of using the pipetter 60 is to collect lymph from the subject, and automatically return it to the subject through an intravenous catheter. This application is very useful to determine whether a tumor is growing, despite the fact that the subject is restrained and is losing his lymph fluid and cells which are, however, being returned to it. After such a test period, the experimental period commences. In this experimental period, the lymph fluid is wasted and the cells are returned.

In another aspect of my new lymph return treatment, one or more donors are used to provide replacement therapy including cell-free lymph (through centrifuge 40) to a subject losing lymph fluid. This results in a decrease in the cost of replacement therapy by a factor of from 10 to 20, depending on the number of donors used. By means of the automatic lymph return system, it is possible to have three donors, for example, supplying lymph to one subject. Under these circumstances, it is likely that the three donors can supply more than enough lymph for the subject without the donors, or their lymph, themselves becoming depleted. Such replacement therapy is cheaper, simpler and more physiologically correct to administer because intermediate stages of packaging, freezing and thawing are eliminated. Such latter steps can introduce sepsis and result in loss of labile compounds necessary for normal health. In that case, the donor lymph can be returned to the donors sequentially through the lymph return system. In all these cases, it is necessary and valuable to know the volume of lymph lost for each subject. This can be done by using the automatic pipetter 60, because the volume of lymph is measured by the number of packages of fluid displacement of the pipette 70. In another aspect of the present invention, production by a subject, of specific antibody, is augmented by the additional step of periodic removal and replacement of the subject's blood, or blood plasma. This additional step prevents the small amount of specific antibody which goes into the subject's blood stream from causing a feedback effect which would ultimately decrease the antibody production caused by the above-described lymphoresis process.

This additional step is taken intermittently, for example about every 10 days, and the removed blood, or blood plasma, is cleansed of the specific antibody being developed, and returned to the subject, or totally replaced by fresh blood free of the specific antibody.

FIGS. 19, 20 illustrate another centrifuge 400 construction especially useful for separating solid particles from a fluid, for example, rat lymph cells from rat lymph fluid. The centrifuge comprises a core member 401, which can be made from aluminum, having a projecting hollow shaft 402 journaled in bearings 403, 404 for rotation about axis 405.

Shaft 402 is driven by conventional means (not shown); a face plate 406 is fastened to the end 407 of core member 401 by conventional fasteners (not shown). The end 407 of core member 401 has a groove 408 cut therein to accommodate fluids carrying tube 409.

One end of the tube 409 is connected to a conventional rotating seal 410, passes through bore 411 of face plate 406 and is laid in groove 408 as shown in FIG. 20. Tube 409 then passes through bore 412 of core member 401 and through the hollow shaft 402 to a second conventional rotating seal 413.

In operation, rat lymph is fed into the centrifuge tube 409 through seal 413. Rotation of core member 401 about axis 405 causes the lymph cells to separate from the lymph fluid at the tube 409 portions lying in circular groove 408a. Washing fluid can be introduced through seal 413, while the cells are separated, to force the lymph fluid from tube 409 out rotating seal 410. The cells and washing fluid can then be removed from the tube 409 out rotating seal 413.

In one embodiment of the centrifuge 400 actually built and successfully operated to separate rat lymph cells from rat lymph fluid, tube 409 was made of polytetrafluoroethylene, had a rectangular cross-section and a width of about 0.030 inch. Core member 401 was made of aluminum and face plate 406 of clear plastic.

Figure 10:
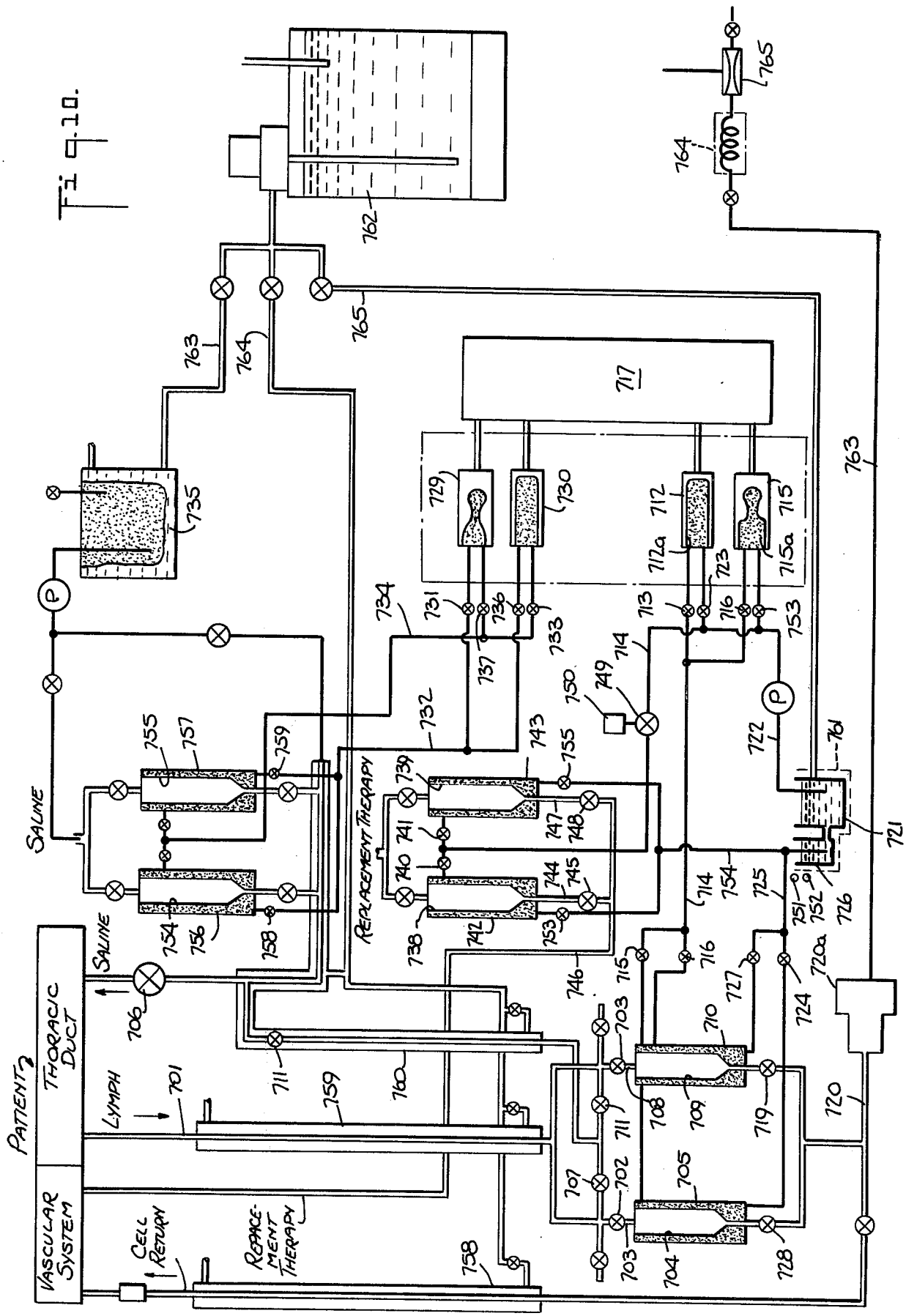
FIG. 10 is a schematic representation of apparatus used in performing the method diagrammed in FIG. 1.

The embodiment of a lymph system in accordance with the invention is shown in FIG. 10. Lymph from the patient is delivered to line 701 which leads to valves 702 and 703. By way of example the rate of delivery of lymph from the patient can be approximately 20 liters per day. The system is designed to accept the flow of lymph from the thoracic duct of the patient without the application of negative or positive pressure to the duct. When valve 702 is opened, line 703 delivers lymph to bag 704 in chamber 705. The bag can be formed of thin flexible material such as silicone rubber.

At the same time a measured amount of saline solution is delivered by line 706 and through valve 706a to the thoracic duct of the patient to dilute and to insure the flow of lymph through pipe 701. By way of example line 706 can deliver a flow of approximately 40 liters per day. When bag 704 is filled, it contains a predetermined quantity of lymph and saline solution and displaces an equal quantity of outer fluid or liquid from the interior of chamber 5.

The system contains a second arrangement of valves and a measuring bag operating in parallel with respect to bag 704. Thus, valve 703 is connected by line 708 to bag 709 mounted in chamber 710. Here it should be noted that all of the lymph and saline solution discharging from the thoracic duct must necessarily pass by way of pipe 701 to either of the bags 704 and 709.

Each of bags 704 and 709 can be alternately operated to deliver the lymph and saline solution therein by the application of fluid to the space within the chamber between the inner wall of the chamber and the outer wall of the bag.

The fluid to be delivered to and thereafter removed from a given chamber is pumped by pumps 712 and 715 which can be pumps of the type known as bellodiaphragm pumps. Thus, pump 712 contains bellodiaphragm 712a, the interior of which is connected by valve 713, line 714 and valve 715 to chamber 705. Similarly, pump 715 contains bellodiaphragm 715a, the interior of which is connected by valve 716 to line 714. Line 714 is also connected by valve 716 to the interior of chamber 709.

Pumps 712 and 715 are actuated by drive 717 which causes one pump to operate on its pressure or pumping stroke while the other pump operates on its suction stroke. As shown in FIG. 10, pump 715 is approaching the end of its pressure stroke with the result that bellodiaphragm 715a is substantially collapsed and has forced the pump fluid or outer fluid through valve 716, line 714 and valve 716 to chamber 710. The introduction of the fluid into chamber 710 causes the progressive squeezing of bag 709 into a collapsed form, thereby discharging the lymph and saline solution from the bag through line 718 and valve 719 to line 720 which leads to the centrifuge 720a of the system. When pump 715 is delivering fluid to chamber 710, valve 703 and valve 711 are closed to block return flow toward the patient and toward line 706 for delivering saline solution. With this arrangement, it can be seen that the volume of bellodiaphragm 715a when pumped to chamber 710 causes a corresponding volume of lymph and saline solution to be ejected from bag 709. It can also be seen that the possibility of contaminating the lymph and saline solution is eliminated since the pumping action of bag 709 is accomplished by the force applied to the bag and without the need for pump constructions having moving pumping elements, seals and the like which could be sources of contamination.

As pump 715 proceeds along its pressure or pumping stroke, pump 712 moves in the opposite direction to effect its suction stroke. The suction stroke of pump 712 results in outer fluid being transferred from reservoir 721 by way of line 722 and valve 723 which communicates with the interior of bellodiaphragm 712a. At the same time, an amount of outer fluid corresponding to that entering bellodiaphragm 712a is forced from chamber 705 by the flow of lymph and saline into bag 704. The outer fluid forced from chamber 705 passes through valve 724, line 725 to chamber 726 which communicates with reservoir 721.

When outer pumping fluid is to be delivered to chamber 705, valve 727 of chamber 710 is opened to enable pumping fluid to pass by way of line 725 to chamber 726. At the same time, valve 728 is open, thereby permitting the lymph and saline solution of bag 704 to be delivered to line 720 and thereby the centrifuge.

It is essential that a balance be maintained between the quantity of lymph being removed from the thoracic duct of the patient and the return of replacement therapy fluid to the patient. For example, if 20 liters a day of lymph are being removed, it is mandatory to return 20 liters per day of replacement therapy fluid to the patient. It is not only essential to maintain a fluid balance on a per day basis but also continually as the lymph is being removed.

The return of replacement therapy is accomplished by bags 738 and 739 which can be of similar construction as bags 704 and 709. Bags 738 and 739 are mounted within chambers 742 and 743, respectively. Line 714 connected to pumps 712 and 715 is coupled by valve 740 to chamber 742 and valve 741 to chamber 743. The return of the flow of outer fluid from chamber 742 is by way of valve 753 to line 754. Chamber 743 is returned to line 754 by way of valve 755.

Flow from bag 738 is directed through line 744 and valve 745 which connects to line 746. Similarly, flow from bag 739 is directed through line 747 and valve 748 to line 746. Line 746 conveys the replacement fluid to the patient.

Whenever one of pumps 712 and 715 are applying outer fluid to line 714, a portion of the fluid is directed by either of valves 740 or 741 to bags 738 and 739, respectively. If, for example, 20 liters per day of lymph is to be received from the patient, each of pumps 712 and 715 must be capable of pumping that amount from bags 704 and 709. In addition, bags 704 and 709 receives a flow of saline which is metered into the thoracic duct.

The total flow of saline into the thoracic duct of the patient as well as into portions of the system in advance of bags 705 and 709 can be, for example, in the amount of about 40 liters per day. If 20 liters per day of lymph as well as 40 liters per day of saline enter bags 705 and 709, it is evident that this amount of outer fluid must be displaced from the chambers 705 and 710. The pumps 712 and 715 must displace outer fluid in an amount corresponding to at least a portion of this total to be displaced from the chambers. For example, pumps 712 and 715 may be selected to pump approximately 40 liters a day. In such an example, the remainder of the total flow of outer fluid, 20 liters a day, would be that related to chambers 742 and 743.

In operation a flow of lymph and saline enters bag 704. The lymph and saline expand bag 704 and cause outer fluid to be displaced through valve 724 into reservoir 721. Pump 712 can receive through valve 723 a portion of flow displaced from reservoir 721 into pipe 722 by the flow from bag 704. Flow from the reservoir not received by pump 712 can flow through pipe 714 along with the fluid being discharged by pump 715. Flow from pipe 714 can be directed by one of valves 740 and 741 to chambers 742 and 743, respectively. The flow into a chamber causes one of bags 738 and 739 to deliver replacement therapy fluid to the patient.

Where, for example, the flow of lymph is 20 liters per day and the flow of saline is 40 liters a day giving a total flow from bags 704 and 709 of 60 liters per day, pumps 712 and 715 can be selected to pump 40 liters a day. The remainder of the 60 liters a day which is not handled by pumps 712 and 715 causes bags 738 and 739 to discharge 20 liters a day. Thus in the example it can be seen that the use of an outer fluid in chambers 704, 705, in chambers 742, 743, and in pumps 712 and 715 insures that replacement fluid equal in amount to the lymph flowing from the patient is returned. Of course it is necessary to control the flow of saline which ultimately enters bags 704 and 709 as will be discussed subsequently.

Flow of lymph and saline into bag 709 leads to a cycle similar to that discussed above. Thus outer fluid is displaced from chamber 710 by bag 709 receiving the flow. The flow of outer fluid can pass through valve 727, reservoir 721 and valve 753 to pump 715. Pump 712 can discharge outer fluid through valve 723 which is coupled to line 714. In this way flow from chamber 710 in part can be displaced into either one of chambers 742, 743.

It is desired to monitor the delivery of replacement fluid on a short term basis and also to administer the fluid at a predetermined rate of delivery. This is accomplished by means of dispensing valve 749 controlled by actuator 750. The actuator is set to cycle valve 749 in a predetermined manner to dispense the replacement fluid in predetermined incremental quantities by controlling the flow of pumping fluid to chambers 742 and 743. For example, the replacement fluid can be periodically delivered in quantities, that is to say packages, in the amount of approximately 5 to 10 ml. per package.

Long term monitoring of the fluid balance of the patient can be accomplished by detecting the level of pumping fluid in chamber 726. For example, photocells 751 and 752 can be employed to sense the level of pumping fluid in chamber 726. Since the pumping fluid is simply being shifted from one of the pair of chambers 705, 710 to one of a pair of chambers 742, 743 and pumps 712, 715, the quantity of pumping fluid in the system is a constant and therefore the level in chamber 726 is constant. If a fault should occur in the pumps or a leak should occur anywhere in the system whether it be a leak of the pumping fluid, the lymph or saline solution being transferred by bags 704 and 709, or the replacement therapy fluid being transferred by bags 738 and 739, a change in the level of fluid in chamber 726 would occur. This would be sensed by photocells 751 or 752 thereby enabling the failure condition to be detected.

Saline is metered to the thoracic duct of the patient as well as to the portion of the system leading toward bags 704 and 709 by bags 754 and 755 disposed in chambers 756 and 757, respectively. The delivery of a predetermined quantity of saline solution to the thoracic duct of the patient or any portion of the system which can flow toward bags 704 and 709 is controlled by pumps 729 and 730 which can also be bellodiaphragm pumps. For example, pumps 729 and 730 can be connected to drive 717 such that these pumps operate in synchronism with pumps 712 and 715, respectively.

As shown in FIG. 10 pump 730 is completing its suction stroke as pump 715 completes its pumping stroke. At such time pump 730 receives outer fluid through valve 736 which is connected to line 732 leading to valves 758 and 759 of chambers 756 and 758, respectively. During the pumping cycle of pump 730, valve 733 delivers outer fluid to line 734 while pump 729 receives outer fluid through line 732 and valve 731. Pump 729 can deliver outer fluid through valve 737 and line 734 to chambers 756 and 757.

This displacement of pumps 729 and 730 is selected to enable the pumps to deliver a predetermined daily quantity of saline solution to the thoracic duct of the patient and portions of the system leading to bags 738 and 739. Since these pumps operate in synchronism with pumps 712 and 715, an accurate balance of the fluids can be maintained. Thus in the example discussed above, pumps 729 and 730 would serve to deliver 40 liters per day of saline solution which together with the 20 liters per day of lymph flowing from the patient comprises the 60 liters per day received by bags 704 and 709.

The valves of the system shown in FIG. 10 can be of the type described heretofore which are capable of being remotely operated and automatically controlled while maintaining a completely sterile condition in all fluids being handled.

In order to control the temperature of the fluids being delivered by the system at least certain of the pipes may be provided with jackets 758, 759 and 760. Similarly, reservoir 721 can be provided with jacket 761. Coolant is transmitted from source 762 by way of lines 763, 764 and 765 to the jackets.

Provision is made to flush the system by fluids such as saline solution from reservoir 735. Valves are provided throughout the system to enable the saline solution to be routed through all portions of the system during a flushing operation.

Line 763 can provide flushing fluid to centrifuge 720a. The flushing fluid can be delivered to line 763 through cooling coil 764. Control of the flow to the coil is provided by valve 765.

REDUCING THE POSSIBILITY OF SEPSIS IN THE APPARATUS

By way of introduction it is noted that bacterial showers often occur in the lymph of normal and more especially diseased subjects. The body can cope with these showers to a large extent. However, if these bacteria were caught or held up in the equipment used for performing my fistula procedure, for any substantial time, they could easily multiply, because lymph is an excellent growth medium for bacteria, and because the bacteria would not be subjected to all the normal defense and bacteria eliminating mechanisms which exist in the body. Excessive bacterial growth or sepsis and the production of endotoxin products from bacteria, can lead to damage or death of lymphocytes contained in the lymph, and serious illness or death of the subject. The following factors maximize against any possible sepsis being generated in the lymph while it is in its extra corporeal circulation during my fistula procedure.

The first consideration is minimization of surface damage to the silicone rubber tubes and containers through which lymph flows. This is important in preventing bacterial "hide-outs" which could act as nidus for infection. Such infection would increase bacterial growth and these bacteria and/or their toxic products, for example endotoxins, can damage the lymphocytes in the extra-coporeal circulation, or can cause pyrogenic reaction, other illnesses or death of the subject.

Accordingly the lymph and introduced Ringers solution termed (inner fluid) only flows from and to the patient through thin walled silicone rubber tubes and containers. The fluid movement through these tubes and containers is controlled under the action of appropriate pumps, for example, FIGS. 12–14, by an outer hydraulic fluid which sequentially squeezes the silicone rubber containers expelling fluid out of them and squeezes silicone rubber tubes resulting in opening and closure of valves. Hydraulic closure of thin walled tubes and containers minimizes surface damage to the material making up the tube or container, because the rubber distorts in a position of minimum stress, that position being the natural configuration the rubber wants to take. In addition, closure of tubes or containers causes stress to the material from which the tubes and containers are made which stress is proportional to the cube of the thickness of the material.

The arrangement of inner fluid contained in thin walled containers and tubes, surrounded by rigid outer jackets which contains the outer fluid, inter alia, has other advantages such as: (a) facilitates the refrigeration of the inner fluid by controlling the temperature of the outer fluid; (b) allows high pressure turbulent washes to charge through the inner compartments (this can occur despite the fact that the inner compartment is made of thin wall material because the pressure load acts only against the outer rigid jacket); (c) turbulent flow through the inner compartment can be greatly increased by rapid fluctuations of the outer compartment volume during the cleaning charges (turbulent flow is necessary to dislodge small clumps and aggregates which attach to the "micro-rough" inner surface of the inner container, because it is known that such clumps and aggregates act as nidus for infection).

A further consideration is the requirement that the inner fluid pass through tubes and containers which are as smooth as possible and which do not have ridges or crevices. It must be noted that lymph is a suspension of cells in a fluid which itself can form aggregates of fibrin or lipo-protein precipitates. Thus the lymph is a slurry of cells in a fluid and a potential slurry of aggregates. In addition, cells or aggregates can initiate cascading reactions which increase further aggregation of cells and fibrin formation.

Figure 16:
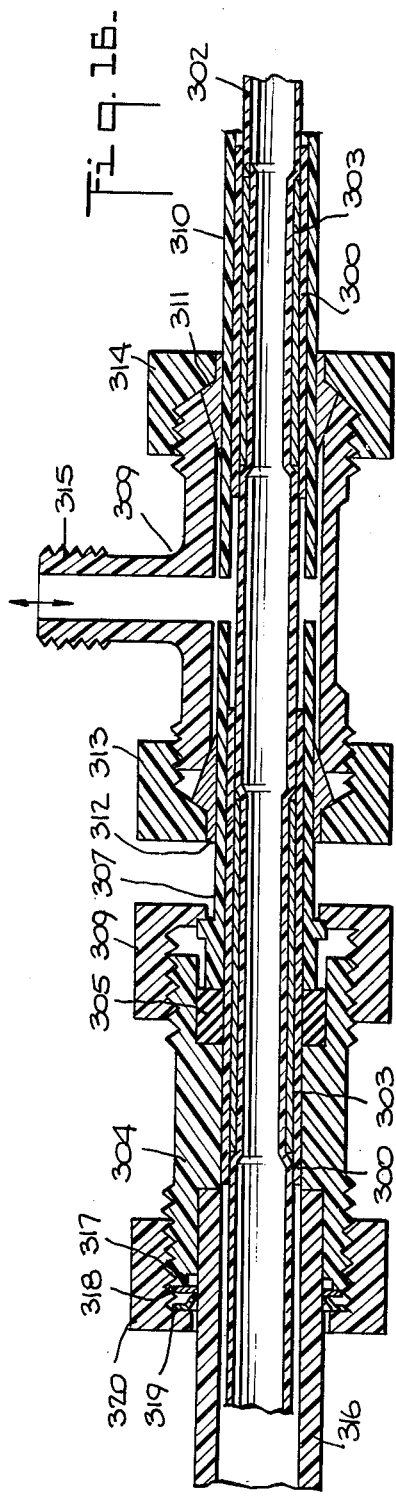
FIG. 16 is a plan section view of another embodiment of squeeze-type valve constructed in accordance with the invention, and having utility in apparatus for performing the procedure diagrammed in FIG. 1.

Accordingly, the entire lymph pathway comprises a smooth, thin wall silicone rubber set of tubes and containers. The construction, for example, of such tubes acting as valves and containers is shown in FIGS. 11, 16 and 15 respectively, described more fully below. It is to be noted that the thin walled flexible inner container is contained within a rigid jacket which itself contains the outer fluid. At several points in the system, it is necessary to make a connection between a thin silicone rubber tube and a rigid polycarbonate tube. To make such a connection without a possible potential crevice (which potential may become a reality under high pressure) between the silicone rubber and the polycarbonate, it is necessary to compress the rubber on to the polycarbonate right up to the very edge of the polycarbonate.

As illustrated in the valves shown in FIGS. 11, 16 this has been achieved by compressing an outer sleeve 300 (FIG. 12) of rubber over the polycarbonate tube 301 and silicone rubber tube 302 where they are co-axially together and beyond the edge of the polycarbonate tube 301. Such compression beyond the edge of the polycarbonate tube 301 can cause distortion of the thin silicone rubber tube 302. This latter distortion is eliminated by placing around the thin silicone rubber tube 32 and just beyond the edge of the polycarbonate tube 301, a tube of aluminum 303.

The outer sleeve 300, when under compression, applies pressure to the silicone rubber tube 302 on polycarbonate tube 301, and just beyond the polycarbonate tube 301, and also on to the aluminum tube 303. If the distance between the end of the aluminum tube 303 and the end of the polycarbonate tube 301 is made short enough, for example a 1/32 inch, it is possible to compress the silicone rubber tube 302 on to the polycarbonate tube 301 right to the edge, without causing distortion of the silicone rubber tube 302 beyond the edge. Such a method of attachment eliminates the potential crevice between the polycarbonate tube 301 and the rubber tube 302.

Referring again to the valve construction illustrated in FIG. 12, the polycarbonate tube 301 can be a modified T-joint, or alternatively a Y-joint (not illustrated). A nylon fitting 304, compressed rubber rings 305, aluminum compression collars 306, 307 and nuts 308, 309 provide compression for the outer silicone rubber sleeve 300. A nylon T fitting 309 is secured to compression collar 307 and polyvinylchloride tube 310 by tapered locking collars 311, 312 and nuts 313, 314. Port 315 of T fitting 309 is coupled to a supply of outer fluid, which when under pressure cuts off the flow of lymph and other fluids through silicone rubber tube 302.

A similar valve construction is illustrated in FIG. 16, where like components are identified by the reference numerals used in FIG. 11. However, in this construction, the valve is connected to a polyvinylchloride tube 316 by means of an O-ring 317, a clamp collar 318, a split steel grip ring or washer 319 and nut 320.

Referring to FIG. 15, the distal end of the thoracic duct catheter 350 is inserted into the upper chamber 351 of a two chamber fluids handling and transfer apparatus. The upper chamber comprises a squeeze valve fitting 352, a bag or container reservoir 353 and a squeeze valve fitting 354. The construction of valve fittings 352, 354 is preferably like that shown in FIGS. 11, 16.

The lower chamber 355 is similarly constructed, and includes squeeze valve fittings 356, 357, 358 and a bag or container-reservoir 359. The containers 353, 359 are made of flexible silicone rubber. The fluids handling and transfer apparatus of FIG. 15 operates as follows.

When fluid is admitted to catheter 350, valves 352, 354, 356 and 357 are open; valves 358 is closed. Accordingly, containers 353, 359 are allowed to fill. When filled, valves 352 and 356 are closed. Fluid can then be sequentially exhausted from containers 353, 359, by opening valve 358 and closing valve 357 to allow admission of outer fluid into the cavity 360, thereby compressing container 359 and forcing the fluid therein out through polyvinylchloride tube 361.

Fluid in the upper container 353 can be transferred to the lower container 359, by closing valve 35, opening valves 356, 357 and closing valve 354 to squeeze the contents of container 353 into container 359. Container 353 can then be refilled by opening valves 352, 354 and closing valve 356.

The apparatus of the kind shown in FIG. 15 can also be used in place of reservoir 12 (FIGS. 1, 12) by connecting a silicone rubber tube 350 to the output 59b of centrifuge 40 (FIG. 3).

Turning again to sepsis considerations, the inner fluid is never allowed to pass through the usual sorts of pumps such as peristaltic pumps, gear pumps, centrifugal pumps. The inner fluid is never allowed to pass through flow meters, liquid level detectors and other equipment because none of such pumps and devices has a smooth fluid path. To control the flow of lymph, and to make appropriate measurements of the flow and volumes of lymph contained in the smooth thin walled inner compartment (for example, containers 353, 359 of FIG. 15), such lymph displaces outer fluid which is the only fluid which passes through the pumps and measuring devices. The outer hydraulic fluid consists of water containing merthiolate as a preservative, benzoic acid as an anti-rust agent and fluorescein as a marker, which can be detected at a concentration of one in a million, should outer fluid burst or leak into the inner compartment.

Moreover, the outer fluid is sterile when the equipment is set up and is maintained sterile by preservatives, refrigeration and continuous passage through a bacterial filter. Furthermore, the outer fluid is only pumped by bellodiaphragm pumps (for example, as shown in FIGS. 13, 14) and magnetically driven gear and centrifugal pumps. Such pumps have the substantial advantage over most pumps in that they do not have packing glans, or O-ring seals, or contact between a moving or a stationary surface. Thus, they are completely "closed" pumps and this eliminates the possibility of introducing sepsis.

Where the outer fluid enters and leaves level detectors, air must be displaced in and out of the system; such displacement takes place through bacterial air filters. Alternatively the level detectors are covered with a thin elastimer which can accept the necessary changes of volume with minimal pressure changes.

Refrigeration of inner and outer fluid is required to minimize bacterial and fungal growth.

Refrigeration is achieved by standard methods such as cooling the major reservoirs, cooling coils, jacketting and maintaining a rapid turn-over rate of cold fluid through the equipment. It is of special importance to refrigerate all filters, because such filters inherently hold up micro-particles of one kind or another and these particles may have bacteria adhered to, or intermeshed within them. In the case of the outer fluid, it is easily possible to arrange that the filter be repeatedly sterilized on-line to prevent the build-up of bacteria. In the case of inner fluid, it is not possible to sterilize the filters on-line and consequently it is necessary to have, in place, a number of such filters in parallel which can be used sequentially.

In addition to the foregoing, build-up of bacteria is prevented by diluting the lymph and increasing the turn-over rate of the inner fluid through the equipment. Large quantities, for example 40 liters/day of cold Ringers solution, which is a balanced salt solution with similar electrolyte composition as body fluid, are continuously infused into the thoracic duct cannula and various parts of the equipment. The Ringers solution increases the turn-over rate of the lymph, its contents and inner fluid all in the extra corporeal equipment, thus decreasing the possibility of bacteria or their products from accumulating and being returned to the subject.

Moreover, the Ringers solution prevents any part of the equipment from becoming a transient stagnant pool of fluid in which bacteria could grow, and cools the lymph. The Ringers solution additionally dilutes the lymph protein and lipo-proteins, which reduces clotting of lymph fluid, precipitation of lipo-proteins and clumping of cells in the lymph. This in important because any such aggregates can act nidus nidue for infection. Furthermore, the Ringers solution assists in washing the cells free of lymph fluid.

The above-described apparatus provides a very rapid turnover of lymph and inner fluid within the extra corporeal circulation. The lymph and inner fluid are moved from place to place, as required, by sequential filling and squeezing the thin silicone rubber tubes and containers, shown in FIGS. 11, 15 and 17 for example. This increases the turnover of inner fluid be a very large factor, for example, a silicone rubber container (353, 359 of FIG. 15 for example) of suitable shape and wall thickness when squeezed at 10 psi leaves only a residual volume of ¼ cc. Let us assume that flow through such a container is at the rate of 50 cc/minute in discrete packages each of 50 cc volume. Each discrete additional volume dilutes the original volume by a factor of 200. Suppose at one time, one of the inner volume fluids contained y number of bacteria which could divide every 10 minutes. After a 10-minute period there will be 2y bacteria but they and their products will have been diluted by 10 successive 50 cc discrete volumes give 10 dilutions each of 200.

In actual practice, such a high level of dilution of bacteria will not be obtained because some of the bacteria may be so tightly bound or emeshed into the surface of the container, that they are not dislodged, and therefore do not enter the general pool of fluid turnover. These bacteria are dislodged by a different method of cleaning, for example, high pressure jets of sterile Ringers solution. The products of bacteria, some of which are toxic, are diluted by the above large factor because they are soluble and move with the general movement of fluid. Those of skill in the art will appreciate that the sequential filling and squeezing of tubes and containers described above, is carried out in such a manner that none of the pressure required for squeezing is transferred to the thoracic duct, since pressure on the thoracic duct would limit the natural egress of lymph and could even rupture the thoracic duct as this latter is made of extremely thin material.

CONTINUOUS MASS IN-VITRO SUSPENSION CULTURE

Turning for the moment to the novel apparatus herein disclosed, because the centrifuge 40 very rapidly separates the cells from the fluid in which they are suspended, and puts them into a very thin, surface layer, this centrifuge has utility in my novel method for the continuous mass in vitro suspension culture of cells. A description of this novel method follows. As used herein, the following terms have the meanings stated. Mammalian and non-mammalian tissues and cells, micro-organisms, and parasites are termed "cells". A culture of cells outside the body of the host is termed "in vitro". When the cultured cells are not attached to a surface, but instead are continuously or intermittently freely suspended and agitated in the culture media, the culture technique is termed "suspension culture". When the number of cultured cells is very large, the culture technique is termed "mass culture". When the culture is continued over a long period of time, for example, days, weeks, or months, the culture technique is termed "continuous culture". Finally, when the culture medium is continuously flowing through the culture chamber, the process is termed "continuous turnover" of culture media.

Mass culture of cells has great utility when a large number of cells, or their products, are required for diagnostic or therapeutic purposes in animals or men.

Mass culture is also of great value to generate cells, or their products, for scientific investigation.

Furthermore, suspension culture is of great value in the art of mass culture, because the environment around every cell is the same, and each cell can derive its nutrition from, and excrete its waste products into, the media surrounding the entire surface of the cell. Furthermore, the agitation process carried on in suspension culture allows a great number of cells per culture chamber to be cultured.

Continuous culture is also of great value, in that a great number of progenies from the original cell population can be generated and collected. Moreover, rapid turnover of the culture media in a continuous turnover process is of great value, because it ensures that the composition of the culture media remains relatively constant throughout the culture period. Constancy of the culture media is a prerequisite to the generation and collection of cells, which have the same growth behaviour and other properties as the original cell population. Collection of cells with constant characteristics is important, if these cells, or products from them, are to be used for scientific investigation or for diagnostic or therapeutic purposes.

Prior to my discovery, mass suspension culture of cells was carried out by agitating the cells and media by various types of stirring rods or movements of the culture chamber. Media was made to flow in and out of the culture chamber. Cells were prevented from leaving the culture chamber by interposing a filter of appropriate pore size in the media exit line. But this procedure has a substantial difficulty in that the filter becomes clogged very quickly. The rate of filter clogging varies with the type of cells being cultured, and the type of culture media which is employed. Clogging is particularly quick, taking only a few minutes, when the culture medium used in such conventional proces consists of fresh flowing cell-free lymph. The clogging filter offers an increasing resistance to the flow of cell-free lymph, ultimately the conventional process inoperative. I have discovered that fresh flowing cell-free lymph has substantial value for certain cultures, for example, Treponema Pallidum, and its use for that purpose is described below.

In accordance with one aspect of my invention, cells are cultured in a centrifuge 40, described above with reference to FIG. 2. The apparatus is programmed to continuously repeat cycles of activity. In accordance with the invention, each cycle consists of various periods.

During the first period, which is termed the centrifugation period, the centrifuge bowl is made to rotate at a rate (RPM) to produce an appropriate gravitational force (G) at the periphery of the bowl, for example, at the inner surface 41. As a result, the cells are held by the force G against the inner surface 41. The size and number of the cells being cultured, and the area of the inner surface 41 of the outer wall of the centrifuge bowl, determines the thickness (T) of the layer of cells during centrifugation.

That portion of the layer of cells in immediate contact with the culture medium has the possibility of obtaining optimum nutrition from the medium. In contrast, the cells in direct contact with the wall 41 of the bowl are covered with a layer of packed cells, and therefore derive their nutrition by a relatively unfavorable process of diffusion through the packed layer of cells. However, since the centrifugation period of the cycle can be of short duration, the unfavorable effect on the latter cells, in any one cycle, can be limited to an insignificant biological extent.

In addition as is described below with reference to the second and third periods, the very nature of the cycling process ensures that a random selection of cells is found in any layer of the subsequently packed cells.

Moreover, the thickness (T) of the packed layer of cells, the duration of the centrifugation period, and the random nature of the cell packing in subsequent cycles, is controlled to limit or eliminate any deleterious biological effect of poor nutrition consequent on cell packing. Eliminating the deleterious biological effects of intermittent cell packing produces culture conditions approximating continuous spinner culture, wherein the cells are continuously in suspension.

During the centrifugation period, a volume of culture medium is pumped through the culture chamber 40a so that there is an almost complete renewal of fresh medium within the chamber 40a. The rate of flow of the medium is as rapid as possible to keep the duration of the centrifugation period as short as possible. The rate of flow is limited, so as not to disturb and move the cells held by gravity. Such movement of cells may result in undesired loss of cultured cells together with the culture medium being pumped out of the chamber 40a. Undesired loss of cells can be reduced or eliminated by appropriate selection of high gravity, low rate of flow, the design of the culture chamber 40a, and the method of pumping the medium, so as to produce laminar flow through the chamber 40a, and eliminate turbulence and pulsations of fluid therein.

The second period of the cycle is called the cell dispersion period. During this period, the flow of culture medium through the culture chamber 40a is stopped, and the input to the culture chamber 40a of the centrifuge 40 is cut off. The culture bowl is now decelerated at a controlled rate. The momentum or kinetic energy of the cultured cells and culture medium, together with the deceleration of the culture bowl causes a controlled relative movement between the bowl and its contents. As a consequence of this movement, the cultured cells are disturbed away from their prior stable position on the inner surface 41 of the outer wall of the bowl, which they occupied during the centrifugation period. The rate of bowl deceleration controls the degree of cell disturbance; this disturbance reaches a level wherein the cells are almost uniformly dispersed in the culture medium.

The third period of the cycle, during which there is no flow of medium through the chamber 40a, is termed maintenance of cell dispersion. I have used two methods to maintain cell dispersion and thus obtain the suspension conditions of the spinner culture techniques.

In the first method, the bowl is rotated about a horizontal axis 43 at a constant low speed to generate a gravitational field, X where X is less than one. Therefore, when the cells are in the lower half of the bowl, they are subjected to endogenous force of $(1 + X) G$, directed towards the periphery of the bowl. When the cells are in the upper half of the bowl, they are subjected to a force of $(1 - X) G$, directed towards the center of the bowl. The continuously changing net gravitation force, which varies both in magnitude and in direction, maintains the cells in suspension in the fresh lymph fluid.

In the second method, the bowl continuously rotates through periods of acceleration and deceleration. Both periods cause relative movement between the contents of the bowl and the bowl itself. There is thus a continuous dispersing effect on the cells, so that they remain in suspension in the fresh lymph fluid throughout this third period.

The fourth period of the cycle is called the cell packing period. During this period, there is no flow of medium through the bowl. The centrifuge bowl is accelerated until it reaches a preselected rotational speed, which is maintained until the cells in suspension are returned to their centrifuged position in a thin layer along the surface of the inner wall 41. It is sometimes of advantage to reduce the gravitational force so generated, to ensure proper packing density, or to maintain that condition properly once the cells have been packed. Reduction of the gravitation force reduces the density of packing and so reduces the difficulty of subsequent dispersement of the cells.

At the end of the fourth period, another cycle is commenced. Periodically a random aliquot of the cultured cells are collected by flowing medium through the culture centrifuge bowl during a period in which the cells are in suspension.

Turning again to my new method for augmenting antibody production, illustrated diagramatically in FIG. 1, in accordance with another aspect of that invention, the above-described novel method for the continuous mass in vitro suspension culture of cells can be adapted continuously to remove specific components, including a specific antibody, from large quantities of fluid, for example, lymph fluid containing the specific antibody.

In this case, the specific antigen, which binds the specific antibody, is attached by various chemical ways to solid substrates, such as cellulose, glass and other materials. The solid substrates are in the form of microparticles so as to increase their surface area, which greatly increases the amount of antigen, and consequently antibody, which they can bind. With respect to this process, it is irrelevant whether the substrate particles have a specific gravity greater or less than the fluid in which the antibody is contained.

The substrate particles with their attached antigen are then introduced into the centrifuge bowl, and the fluid containing the antibody is made to pass through the centrifuge bowl. The substrate particles are alternatively packed or in suspension by repeated periods of gravitational packing and suspension as above described with reference to my method for the continuous mass in vitro suspension culture of cells. In this way, the substrate particles with their attached antigens come into intimate contact with the fluid containing the antibody. This process results in the attachment of the antibody to the antigen, which is itself attached to the substrate particles.

When the antibody binding sites on the substrate particles have been partially or completely saturated, the particles are eliminated from the centrifuge bowl. This can be achieved by flowing a fluid through the bowl, whilst the particles are in suspension. A new fresh quantity of substrate particles with attached antigen is then introduced into the bowl, and the entire process is repeated.

Furthermore, the substrate particles with their attached antigens saturated with antibody can be regenerated so that they can be reused. Regeneration consists of splitting the antigen-antibody complex by various chemical means, such as acid conditions and chaotropic ions, for example, chloride, iodide, bromide. This process not only regenerates the substrate particles, but releases antibody in a high state of purity which is easily collected.

This regeneration process requires the substrate particles to come into intimate, and sequential, contact with various fluids without loss of the particles, until the particles are regenerated. When regenerated, the particles are collected for further use. Moreover, the same process described above for mass culture of cells, and for removing antibody from fluid, is also applicable to the particle regeneration process, because the particles can be made to be repeatedly packed, at which stage new fluid replaces the prior fluid in which the particles were suspended, or suspended, at which stage the particles are in intimate contact with the appropriate fluid.

The foregoing process can also be used to remove a component, for example, erythropoetin (other than antibody), from large quantities of fluid. In this case, the antibody to the desired component is attached to the micro-particles. The antibody removes the component from the fluid medium by attaching it to the micro-particles. The process, including regenerating the particles, is in all other respects identical to the above described process for removing antibody.

Moreover, the same process as above described applies and is useful in many chemical procedures, including biochemical analysis of body fluids for clinical work, for example, as an automatic method of washing precipitates with various solutions.

Furthermore, the above described novel method for the continuous mass in vitro suspension culture of cells has utility as a method for preparing vaccines for active immunization against, for example, Treponema Pallidum, leprosy, and parasites in man and animals.

The first prerequisite for the production of such vaccines, for example, against syphilis, is to be able to culture, on a mass scale, the *Treponema Pallidum* organism in such a way that its antigenicity and other characteristics are not altered. Numerous attempts prior to my discoveries set forth herein, which have only been minor modifications of each other, have failed to achieve this objective. This is almost certainly due to the fact that a suitable culture environment had never been achieved in this prior work. My novel culture technique differs radically from any previous method, since it stimulates the exact environment in which the organism grows inside the body.

In brief summary, in my novel method for producing vaccines, cells and tissues are bathed in extra-cellular fluid. The general composition of this fluid is similar, if not identical, to lymph, and reflects the contributions, both additive and subtractive, or the heterogenous cells which make up the body.

Prior art tissue culture medium, and techniques suffer from two important faults — error in the basic composition of the medium, and its variability from hour to hour and day to day. In accordance with my discovery, the limitations of tissue culture may be overcome, when tissues are grown in unchanged, fresh flowing, cell-free lumph, provided that the system used allows appropriate cellular interactions to occur. The emphasis in my method on unchanged, fresh flowing cell-free lymph reflects the need for constancy of the environment, and the fact that many important regulators of cell activity are labile in blood or lymph.

My basic aim is to grow cells and tissues outside the body, so that they will behave and function in the same manner as tissues growing in the body. The method can also be used to study the growth, behavior, function and response to exogenous and endogenuos agents of various tissues, for example, lymphocytes, lymphoid tissue, bone marrow, thyroid and cancer cells, when they are cultured in unchanged fresh flowing, cell-free lymph; and compare these tissues when they are cultured by standare tissue culture methods.

The in vitro - in vivo culture methods which I have invented depends on a continuous flow centrifuge, for example, of the kind described with reference to FIG. 2, linking the host subject by way of its lymph to the explant tissue or cells. The cell-free lymph fluid is made to pass continuously over the tissue or cells in order to stimulate the extra-cellular fluid turnover of the fluid, which bathes tissues of the body. In the first instance, this requires that a lymphatic vessel of the subject for example, the thoracic duct, be cannulated. Part of the lymphatic flow is then pumped, for example, from a reservoir of the kind described with reference to FIG. 3, into the continuous flow centrifuge 40, and the cell-free lymph intravenously back to the subject.

It is assumed that the composition of the extra-cellular fluid bathing the cells and tissues in the body is identical or nearly identical with the composition of lymph, provided that extra-cellular fluid is generated at a greatly increased rate which rate can be achieved by raised venous pressure of low blood protein concentration. If adequate precautions are taken, it is predicted that there will be minimal changes in the lymph as it flows from the subject through the centrifuge to the growing cells. Because of the complex nature of lymph, the features which have been developed and which are necessary to produce unchanged, or minimally changed, lymph are as follows.

First, the lymph only comes into contact with surfaces which do not denature or alter protein and other macromolecules.

Second, gas-liquid interfaces, and therefore frothing or foaming, are avoided, because it is known that such conditions cause cell destruction and denaturation of proteins. For similar reasons the lymph is not subjected to sudden impacts with a fast moving surface.

Third, all biochemical changes, including those which are likely to occur when a body fluid is in contact with artifactual surfaces, are temperature dependent. The temperature of the lymph is therefore regulated.

Fourth, despite supposedly inert surfaces and control of temperature, it is assumed, in the first instance, that changes in lymph when outside the body proceed as a function of the time the lymph is outside the body. Therefore, the dead space of the centrifuge 40 and ancillary equipment is made as small as possible to minimize the time the lymph is outside the body. One embodiment of centrifuge 40 had a dead space of 2–4 ml. making the time the lymph is outside the body 4–10 minutes. Another embodiment has a larger dead space and because of this, and other reasons inherent in the design, the lymph is outside the body for 15–30 minutes.

Fifth, to avoid contamination of the lymph by products from damaged dying or dead cells, it is essential that the lymph entering the centrifuge 40 does not pass over the packed cells separated from the lymph which had previously entered the centrifuge. This is achieved by centrifuging the cells out of the system after forming them into thin layers along wall 41, cells every 10–15 minutes and returning them to the subject.

Sixth, since the entire system is closed, sterility therefore can be maintained.

Seventh, the pH, $CO_2$ tension and $O_2$ tension are controlled by diffusion of these gases through a length of polytetrafluoroethylene contained in a gas jacket.

Eighth, the temperature of the lymph is not raised significantly as the lymph enters or leaves the centrifuge 40 through the input and output seals 51, 52.

Ninth, the system is able to produce, use and if required return to the subject, the cell-free lymph or the cells contained in the lymph with or without the lymph fluid.

Additional embodiments of my process for bathing tissues and cells with cell-free lymph are as follows: In one embodiment tissues are placed in perfusion chambers and lymph is made to flow through the chamber. This is suitable for tissues which would not be swept away by flowing lymph. Examples are organ, explants, such as endocrine tissue, lymph gland, tooth germ or tumor fragments, lens of the eye, thin sheets of tissue such as omentum, fertilized egg, or dispersed cells which become adherent to the collagenized glass bottom of the chamber.

In another embodiment, lymph is perfused through chambers which have nylon net, for example, about 100 micron mesh, or lens paper or the floor of the chamber. The cells lie on the collangenized glass, and are covered by the nylon net or lens paper, which prevent the cells from being disturbed by the flow of lymph, even though they are not attached to the glass.

In yet another embodiment, the dispersed cells are incorporated into a thin layer of 0.8% agar in perfusion chambers. The lymph is then caused to flow over the top of the agar.

In still another embodiment, a new type of suspension culture is developed. This embodiment has the following features: (a) lymph flows through the culture without losing cells from the culture; (b) controlled, repetitive, intermittent periods of cell dispersion and cell contact are possible, for example, when a mixed population of phagocytes and lymphocytes are cultured, the phagocytes remaining adherent to small glass or plastic spheres, and the lymphocytes alternatively placed in suspension or in contact with the phagocytes; this technique attempts to simulate the life cycle of lymphocytes in vivo which are alternatively free in lymph or blood and are then in contact with phagocytes, and other cells; and (c) easy repetitive sampling of the cultured cells is possible. Briefly, the technique depends upon the availability of a culture chamber rotating around a horizontal axis 43, for example, of the kind described with reference to FIG. 2. The speed of rotation sequentially and automatically is varied to produce about 0.9 G, which develops a gently agitating action to maintain the cells in suspension, and 100 G followed by 5 G, to gently pack the cells together in order to get cell contact. In still another embodiment, the cultured cells are continuously held in a thin layer by a centrifugal force while a thin layer of fresh flowing lymph fluid passes over the cultured cells.

Here follow additional examples of my method for culturing cells and tissues outside the body so that they function, behave and respond to exogenous and endogenous stimuli in the same manner as they do inside the body. In general, these examples are designed to compare tissue growth morphology, enzymatic activity, synthetic ability and response to agents when growing in vitro in standard tissue culture conditions and in fresh flowing cell-free lymph.

EXAMPLE A: Lens of eye.

The lens has been chosen as a model organ for culture, because in vivo it floats in aqueous humor, has no blood supply, derives its nutrition by diffusion, can be removed for culture with minimal trauma, and without disturbing its tissue organization, and because the functional state and viability of its epithelium can be assessed by the transparancy of the lens, and detailed morphological characteristics of its easily mounted epithelium. Such lenses have been successfully cultured by my method.

EXAMPLE B: Bone marrow.

The efficacy of this organ for culture is assessed by colony formation, morphology, ability to incorporate $Fe^{59}$, response to erythropoetin, and the ability of such cultured cells to prevent death of animals, which have received a certain critical dose of irradiation.

EXAMPLE C: Lymphocytes and lymphoid tissues.

Lymphocytes are cultured with, and without, continuous or discontinuous contact with phagocytes and are assessed by morphology, response to antigen and phytohaemagglutinin, and by ability to initiate primary immune response. The immune response is measured by Jerne plaque assay for RBC antigen or modification of Jerne plaque assay for soluble antigen.

EXAMPLE D: Thyroid explants.

The efficacy of this organ for culture is assessed by morphology, uptake of $I^{131}$ (by scintillation counting of tissues whilst in culture and after preparation and radioautographs), by ability to synthesize labelled thyrozine and tri-iodothyronine (chromatography) and by ability to respond to thyroid stimulating hormone.

EXAMPLE E: Tooth germ from 16–18 day old rat or mouse embryo.

The efficacy of this organ for culture is assessed by the capability of developing tooth germ to differentiate histologically.

EXAMPLE F: Enzyme Studies.

Here, it is attempted to culture mammary gland tissue, of heart muscle, and prevent progressive alteration in the activity of various enzymes which uniformaly occur when these tissues are cultured in usual tissue culture medium. The principal technique employed is zone electrophoresis, using hydrolyzed starch gel as the electrophoretic medium. Specific enzyme activities are detected in the gel using histochemical stains. These methods are primarily applicable for the detection of presence or absence of enzyme activities, and are not quantitative procedures. They provide the major advantage of requiring relatively small amounts of material for the detection of large number of enzymes.

The enzymes studied, on both whole tissue extracts and cultured cells, are for example, aldehyde dehydrogenase, octanol alcohol dehydrogenase, a-glycerophosphate dehydrogenase, catalase, acetyl and butyryl esterases, glucose-6-phosphate dehydrogenase, glutamate dehydrogenase, glutamate oxaloacetate transaminase, hexokinase, isocitrate dehydrogenase, lactate dehydrogenase, leucine aminopeptidase, amlate dehydrogenase, peroxidase, acid phosphatase, phosphoglucomutase, 6-phosphogluconate dehydrogenase, succinate dehydrogenase, and tetraxolium oxidase.

In cases where significant quantitative alterations are suggested, as judged by visual inspection of the electrophoretic data, quantitative determinations are carried out by standard analytic techniques.

EXAMPLE G: Cancer Biology.

By way of prefatory comment, critical "indicators" of the identification of neoplastic cells in vitro are lacking. The reasons for this difficulty are: (a) malignant cells from in vivo tumors have difficulty in growing and when and if they do grow, they change in culture; (b) malignancy developing in culture is a malignant change in cells already changed by culture; (c) normal cells change in tissue culture and some of these changes are similar to the characteristics of malignancy; (d) malignancy at present can only be defined with certainty by the ability of the malignant cells to withstand the normal cellular control mechanisms (including immunity) and by the aquisition of properties which enable them to invade and "crush" normal cellular and inter-cellular structures. My novel method is used to determine if malignant cells, cultured in unchanged, fresh flowing cell-free lymph, can be identified by their lack of differentiation, and by their ability to invade normal tissue such as omentum, or thin walled lymphatic vessels. These latter tissues have been chosen, because they are so thin that phase contrast microscopy, and time lapse photomicrography, can be used to observe the interaction between malignant cells and the omentum, or endothelial cells of the lymphatic vessel.

An examination can then be made of the behavior of the cancer cells including the direct action of drugs or antibodies, or both, on malignant tissues growing in an environment provided by my technology. This enables the investigation of the action of cancer chemotherapy drugs on tumor cells, and the possible synergistic action between cancer chemotherapy drugs and immunity against the tumor antigen.

In this regard the following procedures provide valuable data.

First, malignant cells from a patient are grown in his own fresh flowing cell-free lymph. Cancer drugs are infused into the lymph going to each growing chamber. The lymph is not returned to the patient. This helps in predicting which drug would be of most value for the patient.

Second, in addition to the above, the drug is given to the patient. The lymph contains the drug in the same fluctuating concentration as occurs in the extracellular fluid of the patient. This test determines the drug response of the tumor in the patient, and the tumor cells growing in his own lymph.

Third, the cytoxic effect of autologous lymphocytes alone, or together with cancer drugs, on the patient's own tumor provide data on the synergistic action of drugs and immunity.

Furthermore, viruses isolated from human cancers, for example, Burkitt lymphoma may be tested for their ability to induce malignant changes in normal tissue. In the case of Burkitt lymphoma, the target cells for the virus are lymphocytes and their change to malignancy, that is, to become Burkitt target cells, are tested by morphology, immunofluorescent stain, and the ability to grow as a continuous line in tissue culture. It is unlikely that conventional tissues culture methods will be appropriate for testing viruses which may cause Burkitt lymphoma, because lymphocytes do not survive long enough in standard culture medium. The change in lymphocytes to the blast type in standard culture medium is similar to the change which occurs when a lymphocyte becomes Burkitt target cell. The presence of heterologous proteins affects cell morphology, and could interfere with this immunofluorescent examination of those cells. These defects of conventional methods are avoided by tissue culture in accordance with my invention, utilizing unchanged, fresh flowing, cell-free lymph, which when contaminated with virus, is not returned to the donor.

Moreover, it is known that cell-bound antibodies are largely responsible for the rejection of most homografts and tumors; soluble antibody interferes with this action. By passing unchanged, fresh flowing cell-free lymph continuously over growing malignant cells, the soluble antibody against that tumor may be removed by absorption to the growing tumor cells. The antibody is then separated from the tumor cells and can be used for various purposes. The lymph containing all normal components of lymph without such specific antibody is returned to the patient and may allow the rejection of the tumor by the patient's own cell-bound antibody.

The combined use of purified augmented cancer antibody production method, and my method for mass culture of cancer cells in fresh flowing, cell-free lymph, makes possible manufacture of a practical cancer diagnostic kit. A specific patient, known to have a specific cancer is put on my fistula procedure to obtain augmented production of antibodies, including antibodies specific to that cancer. The resulting antibodies can be epurified to any desired degree to segregate the specific-to-cancer antibody, which is then made radioactive and stored under refrigeration to keep it viable.

Moreover, tumor cells are removed from this patient and cultured by my mass suspension method and the resulting culture stored under refrigeration to keep it viable.

Then, the radioactive antibody can be reacted with the cultured cancer cells to determine their interreactions. Once these interreactions are known, unreacted radioactive antibody unreached cultured cancer cells and serum from a subject to be tested for cancer can be mixed. The resulting interreactions will indicate whether the subject has the same cancer or not, because the only components of the subject's serum that could change the standard expected interreaction between the radioactive antibody and the mass cultured cancer cells, are the same specific-to-cancer antibody or the same tumor antigen which components would only be present in the subject's serum, if the subject had the same cancer.

By using my fistula procedures to produce specific-to-cancer antibody and mass culture cancer cells causing production of that antibody, a different diagnostic kit is obtained for each different cancer. The serum samples from a patient being tested for cancer can be subjected to each different diagnostic test, thereby establishing which particular cancer if any the patient has.

It should of course be noted that diagnostic kits for anti-immune diseases of various kinds can be made in the same way.

EXAMPLE H: Reversal of Changes in Cells Cultured in "Standard" Medium

Some of the early changes in tissues consequent on being cultured in "standard" media are partially or completely reversed, when the tissue is transplanted in vivo. In accordance with my invention, the feasibility, nature and biokinetics of this reversal can be studied by incubating the tissue alternatively in tissue culture medium and fresh flowing cell-free lymph. If redifferentiation and repair of enzyme change is achieved in lymph, extensions of such experiments provide data on mechanisms involved in altered genetic expression of tissues. Heart muscle and mammary gland are ideal tissues for this study.

EXAMPLE I: Immunobiology

Up to the present time, the initiation of a primary immune response in vitro has not been completely successful. In accordance with another aspect of my invention, primary antibody formation in lymphoid tissue and lymphocytes is initiated, while they are cultured by my new technique described above. The immune response is then measured as described above in Example C.

If a primary immune response is initiated in lymphocytes, significant data can be obtained regarding: (a) the clonal selection theory; (b) the role of macrophages in the immune response; (c) the morphological and other changes e.g. the incorporation of tritiated thymadine, in cultured cells to determine if they have differentiated with or without mitosis to become antibody producing cells; and (d) the mode of action of antigen overdosage or antibody in inhibiting antibody production.

Furthermore, in respect of applied immunology, if lymphocytes can be maintained in cell-free lymph, and if they snythesize immunoglobins as a response to antigenic stimulation, the following important experiment is performed viz., the culture of lymphocytes, from a prospective recipient of a graft, and attempt to make them synthesize specific immunoglobin against tissues taken from the prospective donor. Such soluble antibodies, called enhancing antibodies, can be collected, concentrated and injected into the recipient on repeated occasions. Such a procedure greatly aids in the prevention of rejection of that graft by the recipient's own cell bound antibodies. This method of prevention of rejection of grafts is not toxic to the recipient, and is superior to the use of immune suppressive drugs, thoracic duct drainage, or extra-corporeal irradiation of blood.

EXAMPLE J: Population Dependency and Clonal Experiments.

By way of prefatory comment, there is a population dependency for growth and function in tissue culture. The need for a critical cell population can be partially or completely overcome by the use of feeder cell layers or conditioned medium. I have discovered that there does not appear to be such a population dependency, when cells are grown in fresh flowing cell-free lymph, whic is in effect a fluid "conditioned" by the contributions of the heterogenous cells of the body. As a result of this discovery, clonal experiments can be performed. For example, a critical examination of the clonal selection theory of immunity can be carried out. Attempts are made to initiate a primary immune response in 1–1000 lymphocytes and phagocytes in each of several culture chambers constructed in accordance with my invention. If each lymphocyte-phagocyte population responds in an identical fashion, it would suggest that all immune reacting cells are equipotential with respect to specific antibody production, and the clonal selection theory would have to be reevaluated.

By way of summary, the in virtro-in vivo technique which I have discovered and described in this application, is a new approach to the study of tissue organization, function and growth. Conventional in vitro and in vivo methods have particular limitations which are strikingly evident in most biological studies of tissues. A bridging of the two traditional methodologies by means of my discoveries, surmounts their respective limitations and provides experimental advantages which may allow many biological problems to be investigated and solved. The detailed experiments set forth in this application, which range from basic studies of cell biology and immuno-biology, to applied studies such as testing possible viruses for their ability to induce tumors in human tissues, represent only a small fraction of the problems that can be successfully studied by my techniques.

While specific embodiments of my invention have been disclosed, variations in procedural and structural detail within the scope of the appended claims are possible and are contemplated. There is, therefore, no intention of limitation to the abstract, or the exact disclosure herein presented.

What is claimed is:

1. A method for the augmentation of production of a specific antibody from a patient which comprises:

selecting a patient making antibodies to a specific antigen selected from the group consisting of endogenous and non-administered exogenous antigens;

performing a thoracic duct fistula on the patient;

raising the patient's central venous pressure to a preselected level to eliminate alternate lymphatico venous channels;

collecting lymph from said fistula;

centrifuging said collected lymph to separate the lymph cells therein from the lymph fluid and to form a thin elongated layer of cells;

treating said thin elongated layer of lymph cells to assure that they are substantially free of the antibody produced by the patient in response to said specific antigen;

dispersing said cells in a physiologically balanced saline solution;

returning said dispersed cells and solution to the patient; and providing replacement therapy to the patient intravascularly.

2. An immunological method which comprises the steps of:

a. selecting a patient making antibodies to a specific antigen selected from the group consisting of endogenous and exogenous antigens;

b. performing a thoracic duct fistula on the patient;

c. raising the patient's central venous pressure to eliminate alternate lymphatico venous channels;

d. collecting lymph from said fistula;

e. centrifuging said collected lymph to separate the lymph cells therein from the lymph fluid and to form a thin elongated layer of said cells;

f. treating said thin elongated layer of lymph cells to assure that they are substantially free of the antibody produced by the patient in response to said specific antigen;

g. dispersing said cells in a physiologically balanced saline solution;

h. returning said dispersed cells and solution to the patient;

i. providing replacement therapy to the patient intravascularly;

j. treating the antibody produced by the patient to separate components thereof; and k. returning at least one of the components to the patient intravascularly.

3. The method according to claim 2 further comprising the steps of treating the antibody produced by the patient to separate the IgG and IgM components thereof, and returning said IgM component to the patients intravascularly.

4. The method according to claim 2 further comprising the steps of treating the antibody produced by the patient to separate the IgG components thereof, collecting a substantial quantity of said IgG component, and returning said quantity of said IgG component to the patient intravascularly.

5. The method according to claim 4 further comprising the step of attaching said IgG component to a member of the group consisting of radioactive compounds, cytotoxic drugs and foreign proteins to which the patient is sensitive, prior to returning said component to the patient.

6. The method according to claim 4 further comprising the step of returning said IgM component to the patient intravascularly.

7. The method according to claim 5 further comprising the step of returning said IgM component to the patient intravascularly.

8. A method for the augmentation of production of a specific antibody from a patient which comprises:

a. administering a specific antigen to said patient to cause production of the specific antibody;

b. performing a thoracic duct fistula on the patient;

c. raising the patient's central venous pressure to eliminate alternate lymphatico venous channels;

d. collecting lymph from said fistula;

e. centrifuging said collected lymph to separate the lymph cells therein from the lymph fluid and to form a thin elongated layer of said cells;

f. treating said thin elongated layer of lymph cells to assure that they are substantially free of the specific antibody produced;

g. dispersing said cells in a lymph fluid physiologically balanced substantially saline solution;

h. returning said dispersed cells and solution to the patient and;

i. providing replacement therapy to the patient intravascularly.

9. A method for the augmentation of production of a specific antibody from a patient which comprises:

a. selecting a patient making antibodies to a specific antigen selected from the group consisting of endogenous and non-administered exogenous antigens;

b. performing a thoracic duct fistula on the patient, c. raising the patient's central venous pressure to eliminate alternate lymphatico venous channels;

d. collecting lymph from said fistula;

e. centrifuging said collected lymph to separate the lymph cells therein from the lymph fluid and to form a thin elongated layer of said cells;

f. treating said thin elongated layer of lymph cells to assure that they are substantially free of the antibody produced by the patient in response to said specific antigen;

g. replacing the separated lymph fluid wth a physiologically balanced saline solution while maintaining said cells in said thin layer;

h. disturbing said thin layer of treated cells to disperse them throughout said solution; and i. returning said dispersed cells and solution to the patient and;

j. providing replacement therapy to the patient intravascularly.

10. The method according to claim 9 further comprising a process for removing said specific antibody from said separated lymph fluid including at least the steps of:

attaching the specific antigen, to which said specific antibody reacts, to a substrate particle;

forming a mixture of said separated lymph fluid and said substrate particles;

centrifuging said mixture to separate said particles from said lymph fluid;

disturbing said separated particles to disperse them throughout said lymph fluid;

maintaining said dispersion for a preselected period of time;

centrifuging said dispersion to again separate said particles from said lymph fluid;

repeating the preceding four steps a preselected number of times to allow attachment of said specific antibody to said substrate attached antigen; and separating said particles from said lymph fluid.

11. The method according to claim 10 wherein said process further includes the steps of chemically treating said separated substrate particles to split the specific antigen-antibody complexes attached thereto, thereby freeing said specific antibodies from said complexes; and separating said freed specific antibodies from said substrate particles.

12. The method according to claim 11 further comprising the step of intravascularly returning to the patient said dispersed lymph cells and specific antibody free lymph fluid with one or more members of the group selected from proteins, sugars, carbohydrates, antibodies, and medicaments, whereby production of the specific antibody in said lymph fluid, flowing from said fistula increases significantly after a short period of time.

13. The method of claim 1 wherein said replacement therapy includes plasma from non-immunized patients of the same species as the patient being treated.

14. The method of claim 2 wherein said replacement therapy includes plasma from non-immunized patients of the same species as the patient being treated.

15. The method of claim 13 wherein said replacement therapy includes pooled serum from non-immunized patients of the same species as the patient being treated.

16. The method of claim 14 wherein said replacement therapy includes pooled serum from non-immunized patients of the same species as the patient being treated.

17. The method of claim 13 further including the steps of raising the central venous pressure of the patient to a preselected level in the range from about 12 to 25 cms. of water pressure to eliminate alternate lymphatico venous channels, than lowering said pressure to about one-half said preselected level, intermittently raising said pressure to said preselected level To assure continued elimination of said alternate channels, and continuously monitoring said pressure to assure that said replacement therapy is not intravascularly returned to the patient when said venous pressure is above said range of pressures.

18. The method of claim 14 further including the steps of raising the central venous pressure of the patient to a preselected level in the range from about 12 to 25 cms. of water pressure to eliminate alternate lymphatico venous channels, then lowering said pressure to about one-half said preselected level, intermittently raising said pressure to said preselected level to assure continued elimination of said alternate channels, and continuously monitoring said pressure to assure that said replacement therapy is not intravascularly returned to the patient when said venous pressure is above said range of pressures.

19. The method of claim 17 wherein the central venous pressure of the patient is raised by surgical procedures.

20. The method of claim 17 wherein the central venous pressure of the patient is raised by intravenous infusions of osmotically active material.

21. The method of claim 18 wherein the central venous pressure of the patient is raised by surgical procedures.

22. The method of claim 18 wherein the central venous pressure of the patient is raised by intravenous infusions of osmotically active material.

23. The method of claim 17 wherein a splenectomy is performed on the patient prior to performing said fistula.

24. The method according to claim 18 wherein a splenectomy is performed on said patient prior to the administration of a specific antigen, and prior to performing said fistula.

25. The method of claim 17 wherein the patient is a member of the group consisting of animals and human beings.

26. The method of claim 18 wherein the patient is a member of the group consisting of animals and human beings.

27. The method of claim 17 wherein the antigen is a member of the group consisting of proteins, infectious agents including viruses and bacteria, cellular antigens including cells containing normal transplantation antigens, cellular antigens including cells containing malignant transplantation antigens, RR Rh antigens, and antigens specific to particular cells or tissues.

28. The method of claim 18 wherein the antigen is selected from the group consisting of proteins, infectious agents including viruses and bacteria, cellular antigens including cells containing normal transplantation antigens, cellular antigens including cells containing malignant transplantation antigens, Rh antigens, and antigens specific to particular cells or tissues.

29. The method of claim 17 wherein the antibody removed from said lymph is removed by removing gammaglobulin.

30. The method of claim 18 wherein the specific antibody removed from said lymph is removed by removing gammaglobulin.

31. The method of claim 2 wherein the antigen is a member of the group consisting of proteins, infectious agents, including viruses and bacteria, cellular antigens including cells containing normal transplantation antigens, cellular antigens including cells containing malignant transplantation antigens, RRRh antigens, and antigens specific to particular cells or tissues.

32. A method for the continuous mass in vitro-in vivo suspension culture of disease organism cells comprising the steps of:
performing a thoracic duct fistula on a patient;
raising the patient's capillary filtration flow by at least one of the steps of raising the central venous pressure or lowering the plastic osmotic pressure, and continuously collecting lymph from said fistula;
centrifuging said collected lymph to separate the lymph cells therein from the lymph fluid and to form a thin elongated layer of said cells;
withdrawing at least a portion of the separated lymph fluid while maintaining said cells in said thin layer;
forming a mixture of cells of a specific disease organism and said withdrawn lymph fluid;
centrifuging said mixture to separate said disease organism cells from said lymph fluid, thereby forming a thin elongated layer of said cells;
replacing said lymph fluid with fresh lymph cell-free lymph fluid collected from the patient;
disturbing said thin layer of disease organism cells to disperse them throughout said fresh lymph fluid;
maintaining said dispersion for a preselected period of time;
centrifuging said dispersion to separate said disease organism cells from said fresh lymph fluid and to form a thin elongated layer of said cells; and
repeating the preceding five steps, in the order given, a preselected number of times to form a mass in vitro suspension culture of said disease organism cells.

33. The method of claim 1 wherein the centrifuging step comprises urging the lymph fluid in to a thin zone at a substantially constant radius from the center of the centrifuging in which zone the lymph cells are distributed into a layer having a thickness which is thin in the order of the cell size, the lymph cells being maintained and distributed in the zone by subjecting all of the lymph fluid to centrifugal acceleration, the thin layer exposing substantially all lymph cells there to the innermost portion of the zone relative to the center of centrifuging to enable all of the cells to be treated and to be treated substantially equally during the centrifuging.

34. The method of claim 1 further comprising the step of administering a specific antigen to said patient to cause production of a specific antibody.

35. The method of claim 1 wherein said replacement therapy includes plasma from non-immunized patients of the same species as the patient being treated.

36. The method of claim 35 wherein said replacement therapy includes pooled serum from non-immunized patients of the same species as the patient being treated.

37. The method of claim 1 wherein the step of raising the central venous pressure of the patient to a preselected level comprises raising the venous pressure to a level in the range from about 12 to 25 cms. of water pressure to eliminate alternate lymphatico venous channels, then lowering said pressure to about one-half said preselected level, intermittently raising said pressure to said preselected level to assure continued elimination of said alternate channels, and continuously monitoring said pressure to assure that said replacement therapy is not intravascularly returned to the patient when said venous pressure is about said range of pressures.

38. The method of claim 1 wherein the central venous pressure of the patient is raised by surgical procedures.

39. The method of claim 1 wherein the central venous pressure of the patient is raised by intravenous infusions of osmotically active material.

40. The method of claim 1 wherein a splenectomy is performed on the patient prior to performing said fistula.

41. The method according to claim 34 wherein a splenectomy is performed on said patient prior to the administration of a specific antigen, and prior to performing said fistula.

42. The method of claim 1 wherein the antigen is selected from the group consisting of proteins, infectious agents including viruses and bacteria, cellular antigens including cells containing normal transplantation antigens, cellular antigens including cells containing malignant transplantation antigens, RR Rh antigens, and antigens specific to particular cells or tissues.

43. The method of claim 1 wherein the antibody removed from said lymph is removed by removing gammaglobulin.

44. The method according to claim 1 further comprising the steps of:
extracting a quantity whole blood from the patient;
administering to the patient a substantially identical quantity of at least one of whole blood and blood plasma, from a non-immunized donor of the same species as the patient being treated; and
periodically repeating the preceding two steps;
thereby reducing the level of concentration of the specific antibody in the blood of the patient.

45. The method according to claim 2 in which the step of treating the separate components of the antibody produced by the patient comprises treating the separate IgG and IgM components.

* * * * *

UNITED STATES PATENT AND TRADEMARK OFFICE
CERTIFICATE OF CORRECTION

PATENT NO. : 3,964,467
DATED : June 22, 1976
INVENTOR(S) : Sam Rose

It is certified that error appears in the above-identified patent and that said Letters Patent are hereby corrected as shown below:

Col. 2, line 47, "field" should be --fluid--;

Col. 9, line 40, delete the word "number";

Col. 10, line 11, "under" should be --number--;

Col. 26, line 7, "be" should be --by--;

Col. 27, line 37, "proces" should be --process--;

Col. 27, line 40, after "ultimately" insert --rendering--;

Col. 28, line 61, delete "endogenous" and substitute --a--;

Col. 30, line 47, start a new paragraph beginning with the word --My--.

Col. 33, line 49, delete "of" and substitute --or--;

Col. 35, line 27, delete "purified" and substitute --my--;

Col. 36, line 38 "snythesize" should be --synthesize--;

Col. 36, line 63 "whic" should be --which--.

Signed and Sealed this

Fifth Day of October 1976

[SEAL]

Attest:

RUTH C. MASON
Attesting Officer

C. MARSHALL DANN
Commissioner of Patents and Trademarks